(12) United States Patent
Tearney et al.

(10) Patent No.: US 7,538,859 B2
(45) Date of Patent: May 26, 2009

(54) METHODS AND SYSTEMS FOR MONITORING AND OBTAINING INFORMATION OF AT LEAST ONE PORTION OF A SAMPLE USING CONFORMAL LASER THERAPY PROCEDURES, AND PROVIDING ELECTROMAGNETIC RADIATION THERETO

(75) Inventors: Guillermo J. Tearney, Cambridge, MA (US); Milen Shishkov, Watertown, MA (US); Brett Eugene Bouma, Quincy, MA (US); Benjamin J. Vakoc, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 21 days.

(21) Appl. No.: 11/670,058

(22) Filed: Feb. 1, 2007

(65) Prior Publication Data
US 2007/0177152 A1   Aug. 2, 2007

Related U.S. Application Data

(60) Provisional application No. 60/764,622, filed on Feb. 1, 2006, provisional application No. 60/810,445, filed on Jun. 1, 2006.

(51) Int. Cl.
*G01L 1/24* (2006.01)
(52) U.S. Cl. .................................................. 356/35.5
(58) Field of Classification Search ................ 356/35.5, 356/450, 484, 485, 496
See application file for complete search history.

(56) References Cited

U.S. PATENT DOCUMENTS 2,339,754 A    1/1944   Brace
(Continued)

FOREIGN PATENT DOCUMENTS

DE    41055221    9/1991
(Continued)

OTHER PUBLICATIONS

Devesa, Susan S. et al. (1998) "Changing Patterns in the Incidence of Esophegeal and Gastric Carcinoma in the United States." *American Cancer Society* vol. 83, No. 10 pp. 2049-2053.

(Continued)

*Primary Examiner*—Michael A Lyons
(74) *Attorney, Agent, or Firm*—Dorsey & Whitney LLP

(57) ABSTRACT

In one exemplary embodiment of the present invention, method and system can be provided for obtaining information associated with at least one portion of a sample. For example, a temperature change can be caused in the portion of the sample. At least one first electro-magnetic radiation can be forwarded to a section near or in the portion of the sample. A deformation of the section can be identified at a plurality of depths as a function of (i) a phase of at least one second electro-magnetic radiation provided from the section, and/or (ii) a rate of change of the phase and/or an amplitude of the second electro-magnetic radiation. In another exemplary embodiment of the present invention, method and system can be provided for controlling a temperature distribution in a sample. For example, an electro-magnetic radiation can be provided to the section in the sample at a particular wavelength. The temperature distribution can be controlled by modifying the particular wavelength of the electro-magnetic radiation when the electro-magnetic radiation is provided to the section.

25 Claims, 17 Drawing Sheets

U.S. PATENT DOCUMENTS

| | | | |
|---|---|---|---|
| 3,601,480 A | 8/1971 | Randall | |
| 3,856,000 A | 12/1974 | Chikama | |
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,141,362 A | 2/1979 | Wurster | |
| 4,295,738 A | 10/1981 | Meltz et al. | |
| 4,300,816 A | 11/1981 | Snitzer et al. | |
| 4,303,300 A | 12/1981 | Pressiat et al. | |
| 4,428,643 A | 1/1984 | Kay | |
| 4,479,499 A | 10/1984 | Alfano | |
| 4,533,247 A | 8/1985 | Epworth | |
| 4,585,349 A | 4/1986 | Gross et al. | |
| 4,601,036 A | 7/1986 | Faxvog et al. | |
| 4,607,622 A | 8/1986 | Fritch et al. | |
| 4,631,498 A | 12/1986 | Cutler | |
| 4,770,492 A | 9/1988 | Levin et al. | |
| 4,868,834 A | 9/1989 | Fox et al. | |
| 4,892,406 A | 1/1990 | Waters | |
| 4,925,302 A | 5/1990 | Cutler | |
| 4,928,005 A | 5/1990 | Lefevre et al. | |
| 4,965,441 A | 10/1990 | Picard | |
| 4,965,599 A | 10/1990 | Roddy et al. | |
| 4,993,834 A | 2/1991 | Carlhoff et al. | |
| 5,039,193 A | 8/1991 | Snow et al. | |
| 5,040,889 A | 8/1991 | Keane | |
| 5,045,936 A | 9/1991 | Lobb et al. | |
| 5,046,501 A | 9/1991 | Crilly | |
| 5,065,331 A | 11/1991 | Vachon et al. | |
| 5,120,953 A | 6/1992 | Harris | |
| 5,127,730 A | 7/1992 | Brelje et al. | |
| 5,197,470 A | 3/1993 | Helfer et al. | |
| 5,202,745 A | 4/1993 | Sorin et al. | |
| 5,228,001 A | 7/1993 | Birge et al. | |
| 5,248,876 A | 9/1993 | Kerstens et al. | |
| 5,262,644 A | 11/1993 | Maguire | |
| 5,291,885 A | 3/1994 | Taniji et al. | |
| 5,293,872 A | 3/1994 | Alfano et al. | |
| 5,293,873 A | 3/1994 | Fang | |
| 5,304,810 A | 4/1994 | Amos | |
| 5,305,759 A | 4/1994 | Kaneko et al. | |
| 5,317,389 A | 5/1994 | Hochberg et al. | |
| 5,321,501 A | 6/1994 | Swanson et al. | |
| 5,353,790 A | 10/1994 | Jacques et al. | |
| 5,383,467 A | 1/1995 | Auer et al. | |
| 5,411,016 A | 5/1995 | Kume et al. | |
| 5,419,323 A | 5/1995 | Kittrell et al. | |
| 5,439,000 A | 8/1995 | Gunderson et al. | |
| 5,441,053 A | 8/1995 | Lodder et al. | |
| 5,450,203 A | 9/1995 | Penkethman | |
| 5,454,807 A | 10/1995 | Lennox et al. | |
| 5,459,325 A | 10/1995 | Hueton et al. | |
| 5,459,570 A | 10/1995 | Swanson et al. | |
| 5,465,147 A | 11/1995 | Swanson | |
| 5,486,701 A | 1/1996 | Norton et al. | |
| 5,491,524 A | 2/1996 | Hellmuth et al. | |
| 5,491,552 A | 2/1996 | Kittrell | |
| 5,526,338 A | 6/1996 | Hasman et al. | |
| 5,562,100 A | 10/1996 | Kittrell et al. | |
| 5,565,986 A | 10/1996 | Knüttel | |
| 5,583,342 A | 12/1996 | Ichie | |
| 5,590,660 A | 1/1997 | MacAulay et al. | |
| 5,600,486 A | 2/1997 | Gal et al. | |
| 5,601,087 A | 2/1997 | Gunderson et al. | |
| 5,621,830 A | 4/1997 | Lucey et al. | |
| 5,623,336 A | 4/1997 | Raab et al. | |
| 5,697,373 A | 12/1997 | Richards-Kortum et al. | |
| 5,698,397 A | 12/1997 | Zarling et al. | |
| 5,710,630 A | 1/1998 | Essenpreis et al. | |
| 5,716,324 A | 2/1998 | Toida | |
| 5,719,399 A | 2/1998 | Alfano et al. | |
| 5,735,276 A | 4/1998 | Lemelson | |
| 5,740,808 A | 4/1998 | Panescu et al. | |
| 5,748,318 A * | 5/1998 | Maris et al. | 356/630 |
| 5,748,598 A | 5/1998 | Swanson et al. | |
| 5,784,352 A | 7/1998 | Swanson et al. | |
| 5,785,651 A | 7/1998 | Kuhn et al. | |
| 5,795,295 A | 8/1998 | Hellmuth et al. | |
| 5,801,826 A | 9/1998 | Williams | |
| 5,803,082 A | 9/1998 | Stapleton et al. | |
| 5,807,261 A | 9/1998 | Benaron et al. | |
| 5,817,144 A | 10/1998 | Gregory | |
| 5,840,023 A | 11/1998 | Oraevsky et al. | |
| 5,840,075 A | 11/1998 | Mueller et al. | |
| 5,842,995 A | 12/1998 | Mahadevan-Jansen et al. | |
| 5,843,000 A | 12/1998 | Nishioka et al. | |
| 5,843,052 A | 12/1998 | Benja-Athon | |
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,920,373 A | 7/1999 | Bille | |
| 5,920,390 A | 7/1999 | Farahi et al. | |
| 5,921,926 A | 7/1999 | Rolland et al. | |
| 5,949,929 A | 9/1999 | Hamm | |
| 5,951,482 A | 9/1999 | Winston et al. | |
| 5,956,355 A | 9/1999 | Swanson et al. | |
| 5,968,064 A | 10/1999 | Selmon et al. | |
| 5,983,125 A | 11/1999 | Alfano et al. | |
| 5,987,346 A | 11/1999 | Benaron et al. | |
| 5,991,697 A | 11/1999 | Nelson et al. | |
| 5,994,690 A | 11/1999 | Kulkarni et al. | |
| 6,002,480 A | 12/1999 | Izatt et al. | |
| 6,004,314 A | 12/1999 | Wei et al. | |
| 6,006,128 A | 12/1999 | Izatt et al. | |
| 6,010,449 A | 1/2000 | Selmon et al. | |
| 6,014,214 A | 1/2000 | Li | |
| 6,033,721 A | 3/2000 | Nassuphis | |
| 6,044,288 A | 3/2000 | Wake et al. | |
| 6,048,742 A | 4/2000 | Weyburne et al. | |
| 6,053,613 A | 4/2000 | Wei et al. | |
| 6,069,698 A | 5/2000 | Ozawa et al. | |
| 6,091,496 A | 7/2000 | Hill | |
| 6,091,984 A | 7/2000 | Perelman et al. | |
| 6,111,645 A | 8/2000 | Tearney et al. | |
| 6,117,128 A | 9/2000 | Gregory | |
| 6,120,516 A | 9/2000 | Selmon et al. | |
| 6,134,003 A | 10/2000 | Tearney et al. | |
| 6,134,010 A | 10/2000 | Zavislan | |
| 6,134,033 A | 10/2000 | Bergano et al. | |
| 6,141,577 A | 10/2000 | Rolland et al. | |
| 6,151,522 A | 11/2000 | Alfano et al. | |
| 6,159,445 A | 12/2000 | Klaveness et al. | |
| 6,160,826 A | 12/2000 | Swanson et al. | |
| 6,161,031 A | 12/2000 | Hochmann et al. | |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,249,349 B1 | 6/2001 | Lauer | |
| 6,263,234 B1 | 7/2001 | Engelhardt et al. | |
| 6,264,610 B1 | 7/2001 | Zhu | |

| | | |
|---|---|---|
| 6,272,376 B1 | 8/2001 | Marcu et al. |
| 6,274,871 B1 | 8/2001 | Dukor et al. |
| 6,282,011 B1 | 8/2001 | Tearney et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,421,164 B2 | 7/2002 | Tearney et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,564,087 B1 | 5/2003 | Pitris et al. |
| 6,564,089 B2 | 5/2003 | Izatt et al. |
| 6,615,071 B1 | 9/2003 | Casscells, III et al. |
| 6,622,732 B2 | 9/2003 | Constantz |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,741,355 B2 | 5/2004 | Drabarek |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,839,496 B1 | 1/2005 | Mills et al. |
| 6,903,820 B2 | 6/2005 | Wang |
| 6,980,299 B1 | 12/2005 | de Boer |
| 7,006,231 B2 | 2/2006 | Ostrovsky et al. |
| 7,231,243 B2 | 6/2007 | Tearney et al. |
| 7,248,907 B2 * | 7/2007 | Hogan ........................ 600/316 |
| 2001/0047137 A1 | 11/2001 | Moreno et al. |
| 2002/0016533 A1 | 2/2002 | Marchitto et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0093662 A1 | 7/2002 | Chen et al. |
| 2002/0122246 A1 | 9/2002 | Tearney et al. |
| 2002/0161357 A1 | 10/2002 | Anderson et al. |
| 2002/0163622 A1 | 11/2002 | Magnin et al. |
| 2002/0172485 A1 | 11/2002 | Keaton et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0023153 A1 | 1/2003 | Izatt et al. |
| 2003/0026735 A1 | 2/2003 | Nolte et al. |
| 2003/0135101 A1 | 7/2003 | Webler |
| 2003/0164952 A1 | 9/2003 | Deichmann et al. |
| 2003/0171691 A1 | 9/2003 | Casscells, III et al. |
| 2003/0199769 A1 | 10/2003 | Podoleanu et al. |
| 2003/0216719 A1 | 11/2003 | Debenedictis et al. |
| 2003/0236443 A1 | 12/2003 | Cespedes et al. |
| 2004/0086245 A1 | 5/2004 | Farroni et al. |
| 2004/0100631 A1 | 5/2004 | Bashkansky et al. |
| 2004/0100681 A1 | 5/2004 | Bjarklev et al. |
| 2004/0133191 A1 | 7/2004 | Momiuchi et al. |
| 2004/0150829 A1 | 8/2004 | Koch et al. |
| 2004/0166593 A1 | 8/2004 | Nolte et al. |
| 2004/0212808 A1 | 10/2004 | Okawa et al. |
| 2005/0018201 A1 | 1/2005 | De Boer |
| 2005/0075547 A1 | 4/2005 | Wang |
| 2005/0083534 A1 | 4/2005 | Riza et al. |
| 2006/0103850 A1 | 5/2006 | Alphonse et al. |
| 2006/0155193 A1 | 7/2006 | Leonardi et al. |
| 2006/0244973 A1 | 11/2006 | Yun et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0590268 | 4/1994 |
| EP | 0933096 | 8/1999 |
| EP | 1426799 | 6/2004 |
| GB | 1257778 | 12/1971 |
| GB | 2030313 | 4/1980 |
| GB | 2209221 | 5/1989 |
| JP | 4135550 | 5/1992 |
| JP | 4135551 | 5/1992 |
| WO | 9219930 | 11/1992 |
| WO | 9303672 | 3/1993 |
| WO | 9533971 | 12/1995 |
| WO | 9628212 | 9/1996 |
| WO | 9732182 | 9/1997 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9905487 | 2/1999 |
| WO | 9944089 | 9/1999 |
| WO | 9957507 | 11/1999 |
| WO | 0058766 | 10/2000 |
| WO | 0108579 | 2/2001 |
| WO | 0138820 | 5/2001 |
| WO | 0142735 | 6/2001 |
| WO | 0236015 | 5/2002 |
| WO | 0238040 | 5/2002 |
| WO | 02054027 | 7/2002 |
| WO | 03020119 | 3/2003 |
| WO | 03052478 | 6/2003 |
| WO | 03062802 | 7/2003 |
| WO | 2004034869 | 4/2004 |
| WO | 20040066824 | 8/2004 |
| WO | 2004088361 | 10/2004 |
| WO | 2004105598 | 12/2004 |
| WO | 2005000115 | 1/2005 |
| WO | 2005054780 | 6/2005 |
| WO | 2005082225 | 9/2005 |
| WO | 20060143392 | 2/2006 |
| WO | 2006130797 | 12/2006 |
| WO | 2007038787 | 4/2007 |

OTHER PUBLICATIONS

Barr, H et al. (2005) "Endoscopic Theorapy for Barrett's Oesophaugs" *Gut* vol. 54:875-884.

Johnston, Mark H. (2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastrorenterology* vol. 112, pages 1787-1797.

Sepchler, Stuart Jon. (1997) "Barrett's Esophagus: Should We Brush off this Balloning Problems?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 5, pp. 1321-1323.

Sharma, P. et al. (2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescene, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, pp. 12-16.

Evans John A. et al. (2006) "Optical Coherence Tomography to Identity Intramucosal Carcinoma and High-Grade Dysplasia in Barrett's Esophagus" *Clinical Gastroenterology and Hepatology* vol. 4, pp. 38-43.

Poneros, John M. et al. (2001) "Diagnosis of Specialized Intestinal Metaplasia by Optical Coherence Tomography" *Gastroenterology* vol. 120, pp. 7-12.

Ho, W. Y. et al. (2005) "115 KHz Tuning Repetition Rate Ultrahigh-Speed Wavelength-Swept Semiconductor Laser" *Optics Letters* Col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagus with High- Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis Precise Microsurgery by Selective Absorption of Pulsed Radiation" *Science* vol. 220. No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation oF burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al. (1992) "Dynamic Optical Property Changes: Implications for Reflectance Feedback Control of Photocoagulation" *Journal of Photochemical,. Photobiology. B: Biol* vol. 16, pp. 113-126.

Deckelbaum, Lawrence I. (1994) "Coronary Laser Angioplaty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W. M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coalulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577nm) Treatment of Port Wine Stains " *Lasers in Surgey and Medicine* vol. 6, pp. 94-99.

French, P.M.W. et al. (1993) "Continuous-wave Mode-Locked $Cr^{4+}$: YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti:$Al_2O_3$ Laser Source" *Optics Letters* vol. 20, No. 13. pp. 1486-1488.

Office Action dated Oct. 11, 2007 for U.S. Appl. No. 11/534,095.

Office Action dated Oct. 9, 2007 for U.S. Appl. No. 09/709,162.

Notice of Allowance dated Oct. 3, 2007 for U.S. Appl. No. 11/225,840.

Siavash Yazdanfar et al., "In Vivo imaging in Blood flow in human retinal vessels using color Doppler optical coherence tomography", SPIE, 1999 vol. 3598, pp. 177-184.

Office Action dated Oct. 30, 2007 for U.S. Appl. No. 11/670,069.

Tang C. L. et al., "Wide-band electro-optical tuning of semiconductor laser", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

Telle M. John, et al., "New method for electro-optical tuning of tunable lasers", Applied Physics Letters, vol. 24, No. 2, Jan.15, 1974, pp. 85-87.

Schmitt M. Joseph et al. "OCT elastography: imaging microscopic deformation and strain of tissue", Optics Express, vol. 3, No. 6, Sep. 14, 1998, pp. 199-211.

M. Gualini Muddassir et al., "Recent Advancements of Optical Interferometry Applied to Medicine", IEEE Transactions on Medical Imaging, vol. 23, No.2, Feb. 2004, pp. 205-212.

Maurice L. Roch et al. "Noninvasive Vascular Elastography: Theoretical Framework", IEEE Transactions on Medical Imaging, vol. 23, No. 2, Feb. 2004, pp. 164-180.
Kirkpatrick J. Sean et al. "Optical Assessment of Tissue Mechanical Properties", Proceedings of the SPIE—The International Society for Optical Engineering SPIE - vol. 4001, 2000, pp. 92-101.
Lisauskas B. Jennifer et al., "Investigation of Plaque Biomechanics from Intravascular Ultrasound Images using Finite Element Modeling", Proceedings of the 19th International Conference—IEEE Oct. 30 - Nov. 2, 1997, pp. 887-888.
Parker K. J. et al., "Techniques for Elastic Imaging: A Review", IEEE Engineering in Medicine and Biology, Nov./Dec. 1996, pp. 52-59.
Dubois Arnaud et al., "Ultrahigh-resolution OCT using white-light interference microscopy", Proceedings of SPIE, 2003, vol. 4956, pp. 14-21.
Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.
Sadhwani, Ajay et al., "Determination of Telfon thickness with laser speckle I. Potential for burn depth diagnosis", Optical Society of America, 1996, vol. 35, No. 28, pp. 5727-5735.
C.J. Stewart et al., "A comparison of two laser-based methods for determination of burn scar perfusion: Laser Doppler versus laser speckle imaging", Elsevier Ltd., 2005, Vol. 31, pp. 744-752.
G. J. Tearney et al., "Atherosclerotic plaque characterization by spatial and temporal speckle pattern analysis", CLEO 2001, vol. 56, pp. 307-307.
PCT International Search Report for Application No. PCT/US2007/068233 dated Feb. 21, 2008.
PCT International Search Report for Application No. PCT/US2007/060787 dated Mar.18, 2008.
Statement under Article 19 and Reply to PCT Written Opinion for PCT International Application No. PCT/US2005/043951 dated Jun. 6, 2006.
PCT International Preliminary Report on Patentability for Application No. PCT/US2005/043951 dated Jun. 7, 2007.
Fernádez, Cabrera Delia et al. "Automated detection of retinal layer structures on optical coherence tomography images ", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics letters, Jul. 15, 2005, vol. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Joo, Chulmin et al., Spectral-domain optical coherence phase microscopy for quantutative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissue and Collagen by Means of Brillouin Light Scattering", Connective Tissue Research, 1990, vol. 24, pp. 187-205.
Berovic, N. "Observation of Brillion scatering from single muscle fibers", European Biophysics Journal, 1989, vol. 17, pp. 69-74.
PCT International Search Report and Written Opinion for Application No. PCT/US2007/062465 dated Aug. 8, 2007.
Pyhtila John W. et al., "Rapid, depth-resolved light scattering measurements using Fourier domain, angle-resolved low coherence interferometry", Optics Society of America, 2004.
Phytila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Marsh/Apr. 2006, pp. 0210061-1 -0210061-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optical Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
Fujimoto et al., "High Resolution in Vivo Intra-Arterial Imaging with Optical Coherehence Tomography," *Official Journal of the British Cardiac Society*, vol. 82, pp. 128-133 Heart, 1999.
D. Huang et al., "Optical Coherence Tomography," *Science*, vol. 254, pp. 1178-1181, Nov. 1991.
Tearney et al., "High-Speed Phase—and Group Delay Scanning with a Grating Based Phase Control Delay Line," *Optics Letters*, vol. 22, pp. 1811-1813, Dec. 1997.
Rollins, et al., "In Vivo Video Rate Optical Coherence Tomography," *Optics Express*, vol. 3, pp. 219-229, Sep. 1998.
Saxer, et al., "High Speed Fiber-Based Polarization-Sensitive Optical Coherence Tomography of in Vivo Human Skin," *Optical Society of America*, vol. 25, pp. 1355-1357, Sep. 2000.
Oscar Eduardo Martinez, "3000 Times Grating Compress or with Positive Group Velocity Dispersion," *IEEE*, vol. QE-23, pp. 59-64, Jan. 1987.
Kulkarni, et al., "Image Enhancement in Optical Coherence Tomography Using Deconvolution," *Electronics Letters*, vol. 33, pp. 1365-1367, Jul. 1997.
Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Imges," *Journal of Biomedical Optics*, vol. 4, pp. 125-136, Jan. 1999.

Tearney, et al., "In Vivo Endoscopic Optical Biospy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., "A Portable, Low Coherence Interferometry Based Instruments, for Fine Needle Aspiration Biopsy Guidance," *Accepted to Review of Scientific Instruments*, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Laser and Amplifiers," *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal Of Lightwave Technology*, vol. 7, pp. 3-10, Jan. 1989.

Beaud, P. et al., "Optical Reflectometry with Micrometer Resolution for the Investigation of Integrated Optical-Devices," *Ieee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E, et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Sources," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf"Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fuji, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Reciever," *Journal of Lightwave Technology*, vol. LT-5, p. 274, Feb. 1987.

Glombitza, U., "Coherent Frequency-Domain Reflectometry for Characterization of Single-Mode Integrated-Optical Wave Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol., 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, pp. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier" Applied Physics Letters, vol. 51, pp. 1051-1053, 1987.

Ivanov, A.P. et al., "New Method for High-Range Resolution Measurements of Light Scattering in Optically Dense Inhomogeneous Media," *Optics Letters*, vol. 1, pp. 226-228, Dec. 1977.

Ivanov, A.P. et al, "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbin Media: Effective Receiver Size at Optical Through Millimeter Wavelengths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerial Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi, Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues By Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurement Using Modulation of the Spectrum of White-Light in a Michelson Interfereometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, 1404-1406, Dec. 1992.

Swanson, E. A. et al., "High-Speed Optical Coherence Domain Reflectometry," Optics Letters, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May, 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal Of Quantum Electronics*, vol. 17, pp. 404-407, Mar. 1981.

Toide, M et al., "Two-Dimensional Coherent Detection Imaging in Multiple Scattering Media Based the Direrctional Resolution Capability of the Optical Heterodyne Method," *Applied Physics B (Photophyscis and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbrium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 13, pp. 1087-1096, Aug. 1997.

Yun, S. H. et al., "Interrogation of Fiber Grating Sensor Arrays with a Wavelength-Swept Fiber Laser," *Optics Letters*, vol. 23, pp.843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wong, Brian J.F. et al., "Optical Coherence Tomography of the Rat Cochlea," *Journal of Biomedical Optics*, vol. 5, No. 4, Oct. 2000, pp. 367-370.

Yao, Gang et al., "Propagation of Polarized Light in Turbid Media : Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissued by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Senitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No.3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography" *Journal of Biomedical Optics*, vol. 7, No. 3, Jul. 2002, pp. 350-358.

Kursnov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarization-Sensitive Optical CoherenceTomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.

Zhang, Jun et al., "Determination of Birefringence and Absolute Optic Axis Orientating Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al., "Variation of Peripapillary Retinal Nerve Fiber Layer Birefringence in Normal Human Subjects," *Investigative Opthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Opitcal Coherence Tomography Imaging for Dermatology," *The Society for Investigating Dermatology, Inc*. 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al., (1991). "Femtosecond Temporal Encoding in Barium-Titanate." *Optics Letters* 16(24):1984-1986.

Aigouy, L., A. Lahrech, et al., (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D.P. Dave, et al. (2004). "Detection of neural activity using phase-sensitive optical low-coherence reflectometry." *Optics Express* 12(11):2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurement of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6):845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermal Mediated Therapeutic Procedures." *Physics in Medical and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medical and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13):958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A, H., Gerd; Herrmann, Juergen M.; Lindner, Michael W.; Ringler, R. (1996). "Optical coherence tomography with the "spectral radar": fast optical analysis in volume scatters by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent Optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3):159-161.

Barakat, R. (1993). "Analytic Proofs of the Arago-Fresnel Laws for the Interference of Polarized-Light." *Journal of the Optical Society of America a-Optics image Science and Vision* 10(1): 180-185.

Barbastathis, G. and D. J. Brady (1999). "Multidimensional tomographic imaging using volume holography." *Proceedings of the Ieee* 87(12):2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J.K., A. Rollins et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography; a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescene microscopy." *Optics Letters* 24(14): 969-971.

Bechara, F. G., T. Gambichler, et al. (2004). "Histomorpholgic correlation with routine histology and optical coherence tomography." *Skin Research and Technology* 10 (3): 169-173.

Bechmann, M., M. J. Theil, et al. (2000). "Central corneal thickness determined with optical coherence tomography in various types of glaucoma. [see comments]." *British Journal of Ophthalmology* 84(11):1233-7.

Bek, T. and M. Kandi (2000). "Quantitative anomaloscopy and optical coherence tomography scanning in central serous chorioretinopathy." *Acta Ophthalmologica Scandinavica* 78(6):632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter" *Physical Review* E 49(2): 1767-1770.

Blanchot,L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45 (Suppl 3): S305-12; discussion S332-4.

Blumenthal, E. Z., J. M. Willaims, et al. (2000). "Reproducibility of nerve fiber layer thickness measuremnets by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Foward-imaging instruments for optical coherence tomogaphy." *Optical Letters* 22.

Boppart, S. A., B. E. Bouma, et al. (1998). "Intraoperative assement of microsurgery with three-dimensional optical coherence tomography." Radiology 208: 81-86.

Boppart, S. A., B. E. Herrmann, et al. (1999). "High-resolution optical coherence tomogrpahy-guided laser ablation of surgical tissue." Journal of Surgical Research 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997)."Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evalution of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." Optics Letters 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophtalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effect of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artey microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E. G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1998). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review E* 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585..

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micromter Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissues using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescenence Microscopy." *Science* 248(4951): 73-76.

Descour, M. R., A. H. O. Karkkainen, et al. (2002). "Toward the development of miniaturized Imaging systems for detection of precancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Sturcture and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in occur media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [eratum appears in Nat Med 2001 May;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Foreman and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatters." Proceedings of SPIE—The International Society for Optical Engineering 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evalution of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The international Society for Optical Engineering.

Fercher, A. F., W. Drexler, et al. (2003). "Optical coherence tomography —principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. Hitzenberger, et al. (1996). *Ocular partial coherence interferometry*. Proceedings of SPIE—The International Society for Optical Engineering.

Fercher, A. F., C. Hitzenberger, et al. (1993). "In-Vivo Optical Coherence Tomography." *American Journal of Ophthalmology* 116(1): 113-115.

Fercher, A. F., C. Hitzenberger, et al. (1994). *In-vivo dual-beam optical coherence tomography* Proceedings of SPIE—The International Society for Optical Engineering.

Fercher, A. F., C. Hitzenberger, et al. (1995). "Measurement of Intraocular Distances by Backscattering Spectral Interferometry." *Optics Communications* 117(1-2): 43-48.

Fercher, A. F., C. Hitzenberger, et al. (2000). "A thermal light source technique for optical coherence tomography." *Optics Communications* 185(1-3): 57-64.

Fercher, A. F., C. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., Haelterman, et al. (1991). "All-Optical Polarization Switch with Long Low-Birefringence Fiber." *Electronics Letters* 27916): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002)."Optical coherence tomography of choridal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination. " *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabue (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical plannig with magnetic resonance imaging-based 3-dimensional reconstructions for intralesional Nd: YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 16976-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forsetefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). " The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (20030. "Macular thickness changes in glaucomatous optic neuropathy detected using optical coherence tomography." *Archives of Ophthalmology* 121(1): 41-46.

Greenfield, D. S., R. W. Knighton, et al. (200). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical Coherence tomography measurement of macular and nerve fiber layer thickness in normal and glaucomatous human eyes." *Ophthalmology* 110(1): 177-189.

Guegniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." Journal of Cell Science 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogenous and Coated Spheres." 1-11.

Haberland, U. B., Vladimir, Schmitt, Hans J. (1996). "Optical coherent tomography of scattering media using electrically tunable near-infrared semiconductor laser." *Applied Optics* Draft.

Haberland, U. W., Walter; Blazek, Vladimir, Schmitt, Hans J. (1995). "Investigation of highly scattering media using near-infrared continous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Tranfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatters with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomogaphy." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K., and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dematology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris. (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. And R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojitkowski, et al. (2005). "Amplified frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. 2001 Sep;132(3):458-61; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner et al. (2002). " Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkarni, et al. (1997). "In vivo bidirectional color Doppler flow imaging of picoliter blood volumes using optical coherence tomography." Optics Letters 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31 (7): 488-493.

Jones, R. C. (1942). "A new calculus for the treatment of optical systems. IV." *Journal of the Optical Society of America* 32(8): 486-493.

Jones, R. C. (1947). "A New Calculus for theTreatment of Optical Systems . 6. Experimental Determination of the Matrix." *Journal of the Optical Society of America* 37(2): 110-112.

Jones, R. C. (1947). "A New Calculus for theTreatment of Optical Systems .5. A More General Formulation, and Description of Another Calculus." *Journal of the Optical Society of America* 37(2): 107-110.

Jones, R. C. (1948). "A New Calculus for theTreatment of Optical Systems .7. Properties of the N-Matrices." *Journal of the Optical Society of America* 38(8): 671-685.

Jones, R. C. (1956). "A New Calculus for theTreatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomography to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41 (3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W. and X. R. Huang, et al. (2002). "Analytical methods for scanning laser polarimetry for retinal nerve fiber layer assessment." *Investigative Ophthalmology & Visual Science* 43(2): 383-392.

Knuettel, A. R. S., Joseph M.; Shay, M.; Knutson, Jay R. (1994). "Stationary low-coherence light imaging and spectroscopy using a CCD camera." *Proc. SPIE*, vol. 2135: pp. 239-250.

Knuettel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuettel, A. and M. Schmitt (1993). "Stationary Depth-Profiling Reflectometer Based on Low-Coherence Interferometry." *Optics Communications* 102(3-4): 193-198.

Knuettel, A. and M. Schmitt, et al. (1994). "Low-Coherence Reflectometry for Stationary Lateral and Depth Profiling with Acoustooptic Deflectors and Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanai, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progeression from ocular hypertension to primary open angle glaucoma." *Clin Experiment Ophthalmogy* 30(4): 242-7.

Laszlo, A. Venetianer (1998). Heat resistance in mammalian cells: Lessons and challenges. *Stress of Life*. 851: 169-178.

Lazlo, A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 286-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetter, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetter, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see Comments]." *Archives of Ophthalmolgy* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26; 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evalution of skin subjected to instantaneous heating." *IEEE Transactions on Biomedical Engineering* 46(4): 420-8.

Luke, D. G., R. McBride, et al. (1995). "Polarization mode dispersion minimization in fiber-woound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11 (3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (9184). "Negative Group-Velocity Dispersion Using Refraction." *Journal of the Optical Society of America a-Optics Image Science and Vision* 1 (10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical abiltiy of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." Physics in Medicine and Biology 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmolgy* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy--1976 to 1995." *Ophthalmolgy* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. Mckay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G. W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-774.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dipersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomography and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatters." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1998). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode laser." *Optics Letters* 24(4): 238-240.

Simon, R. (1982). "The Connection between Mueller and Jones Matrices of Polarization Optics." *Optics Communications* 42(5): 293-297.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optics acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimaura, et al. (1994). "Optical Multimode Frequency-Domain Reflectometer." *Optics Letters* 19(8): 587-589.

Tan-no, N., T. Ichimaura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherenece tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2001). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." *Optics Communications* 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of Xenopus laevis." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-reference Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength- swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral- domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. Chen, et al. (2000). "Doppler standard deviation imaging for clinical monitoring of in vivo human skin blood flow." *Optics Letters* 25(18): 1358-1360.

Zhao, Y. H., Z. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibera", *Journal of Lightwave Technology* 1997, 15 (10): 1842-1851.

Tsuyoshi Sonehara et al. "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE* 1999, 2979:468-477.

David J. Briers, "Speckle fluctuations and biomedical optics: implications and applications", Optical Engineering, 1993, 32(2):277-283.Clark et al., "Tracking Speckle Patterns with Optical Correlation", SPIE, 1992, 1772:77-87.

Clark et al., "Tracking Speckle Patterns with Optical Correlation", SPIE 1992, 1772:77-87.

Facchini et al., "An endoscopic system for DSPI", Optik, 1993, 95(1):27-30.

Hrabovsky, M., "Theory of speckle dispacement and decorrelation: application in mechanics", SPIE, 1998, 3479:345-354.

Sean J. Kirkpatrick et al., "Micromechanical behavior of cortical bone as inferred from laser speckle data", Journal of Biomedical Materials Research, 1998, 39(3):373-379.

Sean J. Kirkpatrick et al., "Laser speckle microstrain measurements in vascular tissue", SPIE, 1999, 3598:121-129.

Loree et al., "Mechanical Properties of Model Atherosclerotic Lesion Lipid Pools", Arteriosclerosis and Thrombosis, 1994, 14(2):230-234.

Podbielska, H. "Interferometric Methods and Biomedical Research", SPIE, 1999, 2732:134-141.

Richards-Kortum et al., "Spectral diagnosis of atherosclerosis using an optical fiber laser catheter", American Heart Journal, 1989, 118(2):381-391.

Ruth, B. "blood flow determination by the laser speckle method", Int J Microcirc: Clin Exp, 1990, 9:21-45.

Shapo et al., "Intravascular strain imaging: Experiments on an Inhomogeneous Phantom", IEEE Ultrasonics Symposium 1996, 2:1177-1180.

Shapo et al., "Ultrasonic displacement and strain imaging of coronary arteries with a catheter array", IEEE Ultrasonics Symposium 1995, 2:1511-1514.

Thompson et al., "Imaging in scattering media by use of laser speckle", Opt. Soc. Am. A., 1997, 14(9):2269-2277.

Thompson et al., "Diffusive media characterization with laser speckle", Applied Optics, 1997, 36(16):3726-3734.

Tuchin, Valery V., "Coherent Optical Techniques for the Analysis of Tissue Structure and Dynamics," Journal of Biomedical Optics, 1999, 4(1): 106-124.

M. Wussling et al., "Laser diffraction and speckling studies in skeletal and heart muscle", Biomed, Biochim, Acta, 1986, 45(1/2):S 23- S 27.

T. Yoshimura et al., "Statistical properties of dynamic speckles", J. Opt. Soc. Am A. 1986, 3(7): 1032-1054.

Zimnyakov et al., "Spatial speckle correlometry in applications to tissue structure monitoring", Applied Optics 1997, 36(22): 5594-5607.

Zimnyakov et al., "A study of statistical properties of partially developed speckle fields as applied to the diagnosis of structural changes in human skin", Optics and Spectroscopy, 1994, 76(5): 747-753.

Zimnyakov et al., "Speckle patterns polarization analysis as an approach to turbid tissue structure monitoring", SPIE 1999, 2981:172-180.

Ramasamy Manoharan et al., "Biochemical analysis and mapping of atherosclerotic human artery using FT-IR microspectroscopy", Atherosclerosis, May 1993, 181-1930.

N. V. Salunke et al., "Biomechanics of Atherosclerotic Plaque" Critical Reviews™ in Biomedical Engineering 1997, 25(3):243-285.

D. Fu et al., "Non-invasive quantitative reconstruction of tissue elasticity using an iterative forward approach", Phys. Med. Biol. 2000 (45): 1495-1509. **

S. B. Adams Jr. et al., "The use of polarization sensitive optical coherence tomography and elastography to assess connective tiisue", Optical Soc. of American Washington 2002, p. 3.**

Erdelyi et al. "Generation of diffraction-free beams for applications in optical microlithography", J. Vac. Sci. Technol. B 15 (12), Mar/Apr 1997, pp. 287-292.

Tearney et al., "Spectrally encoded miniature endoscopy" Optical Society of America; Optical Letters vol. 27, No. 6, Mar.15, 2002; pp. 412-414.

Yelin et al., "Double-clad Fiber for Endoscopy" Optical Society of America; Optical Letters vol. 29, No. 20, Oct. 16, 2005; pp. 2408-2410.

PCT International Preliminary Report on Patentabilty for International Application No. PCT/US2004/038404 dated Jun. 2, 2006.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162. **

A. Ymeti et al., "Integration of microfluidics with a four-channel integrated optical Young interferometer immunosensor", Biosensors and Bioelectronics, Elsevier Science Publishers, 2005, pp. 1417-1421. **

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography Gastrointestinal Endoscopy clinics of North America", 14 (2004) pp. 573-588. **

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474. **

Ko T et al., "Ultrahigh resolution in vivo versus ex vivo OCT imaging and tissue preservation", Conference on Lasers and electro-optics, 2001, pp. 252-253. **

Paul M. Ripley et al., "A comparison of Artificial Intelligence techniques for spectral classification in the diagnosis of human pathologies based upon optical biopsy", Journal of Optical Society of America, 2000, pp. 217-219. **

Wolfgang Drexler et al., "Ultrahigh-resolution optical coherence tomography", Journal of Biomedical Optics Spie USA, 2004, pp. 47-74. **

PCT International Search Report for Application No. PCT/US2006/016677 filed Apr. 28, 2006.

International Wriiten Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report for Application No. PCT/US2004/023585 filed Jul. 23, 2004.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.********

Lauer, V. "New approach to optical diffraction tomography yielding a vector equation of diffraction tomography and a novel tomographic micrographic microscope", Journal of Microscopy vol. 205, Issue 2, 2002, pp. 165-176. ********

Yu, P. et al. "Imaging of tumor necrose using full-frame optical coherence imaging", Prcoeedings of SPIE vol. 4956, 2003, pp. 34-41. ********

Zhao, Y. et al. "Three-dimensional reconstruction of in vivo blood vessel in human skin using phase-resolved optical Doppler tomography", IEEE Journal of Selected Topics in Quantum Electronics 7.6 (2001): 931-935. ********

Office Action dated DEc. 18, 2006 for U.S. Appl. No. 10/501,276.

* cited by examiner

Prior Art

METHODS AND SYSTEMS FOR MONITORING AND OBTAINING INFORMATION OF AT LEAST ONE PORTION OF A SAMPLE USING CONFORMAL LASER THERAPY PROCEDURES, AND PROVIDING ELECTROMAGNETIC RADIATION THERETO

CROSS-REFERENCE TO RELATED APPLICATION(S)

This application is based upon and claims the benefit of priority from U.S. Patent Application Ser. No. 60/764,622, filed Feb. 1, 2006 and U.S. Patent Application Ser. No. 60/810,445, filed Jun. 1, 2006, the entire disclosures of which are incorporated herein by reference.

STATEMENT REGARDING FEDERALLY SPONSORED RESEARCH

The invention was made with the U.S. Government support under Contract No. 17-02-2-0006 awarded by the US Department of the Army Cooperative Agreement (DAMD). Thus, the U.S. Government has certain rights in the invention.

FIELD OF THE INVENTION

The present invention relates to systems and methods for monitoring at least one portion of a sample using conformal laser therapy procedures, providing electromagnetic radiation thereto and obtaining information associated with at least one characteristic of the sample.

BACKGROUND OF THE INVENTION

A use of lasers for ablating or thermally destroying diseased tissue is known and at time preferred, primarily due to the potential for precise local effect with minimal collateral damage. In practice, however, laser therapy has been less than perfect for use in certain clinical applications, such as the treatment of early epithelial cancers and their precursors. One of the problems with laser therapy for these applications has been the inability to accurately control and guide the treatment depth, resulting in either disease recurrence due to incomplete therapy or complications associated with overly aggressive treatment.

Epithelial Cancer: Diagnosis and Treatment

Methods and techniques for identifying and treating cancer at an early stage have been widely pursued as offering the potential to dramatically decrease the morbidity and mortality associated with metastasis. Since epithelial cancers and precursor lesions are frequently focal and can be distributed heterogeneously across a wide field, a sensitive diagnosis is extremely demanding. A diagnosis should be rendered on the size scale of a single cell in a field comprising possibly more than a billion cells.

Epithelial cancer also presents challenges for therapy. Since they are superficial, access to epithelial lesions can frequently be obtained through the use of minimally invasive catheters or endoscope. The therapeutic challenge, however, is in comprehensively killing, resecting or ablating the entire lesion without damage to underlying or adjacent tissues. This is particularly challenging since the depth of disease and even the thickness of normal epithelial layers can vary substantially. Additionally, epithelial tissues are highly compliant and therapeutic instrumentation can result in significant compression. As a result, therapies designed to affect tissue to a fixed depth risk either under-treatment resulting in recurrence, or over-treatment that can lead to significant complications.

Barrett's Esophagus

The importance of Barrett's esophagus (BE) is based primarily on the prevalence of this disease, the rapid increase in its incidence, and the dismal prognosis for patients with high-grade dysplasia and adenocarcinoma. as described in publication 1 identified below. The current consensus (as described in publications 2 and 3 identified below) holds that comprehensive destruction of BE in a controlled fashion, along with anti-reflux treatment, results in squamous regrowth and that continued reflux control prevents the return of BE. The challenge is in achieving comprehensive removal of the pathologic mucosa, while preserving the underlying tissues of the esophageal wall. Treatment that is incomplete can result in a squamous overgrowth that masks underlying pathology. Overly aggressive therapy can result in stricture or perforation of the esophageal wall. Provided below is the information relating to screening and therapy of BE.

Screening

Several approaches for esophageal screening in the management of BE have been investigated. Brush cytology (as described in publications 4 and 5 identified below) and the use of biological markers, such as the deletion and/or mutation of the 17p (p53) gene, (as described in publications 6 and 7 identified below) can be used independently of endoscopy but cannot provide spatial mapping of disease. High magnification video endoscopy (as described in publication 8 identified below), fluorescence spectroscopy (as described in publications 9 identified below), and light-scattering spectroscopy (as described in publications 10 identified below) each show promise for point diagnoses, but provide insufficient information regarding subsurface microstructure and have not been demonstrated for wide-field screening. High-resolution endoscopic ultrasound and chromoendoscopy (as described in publications 11 and 12 identified below, respectively) can both be applied to a wide field, but have suffered from low sensitivity and specificity.

Optical coherence tomography (OCT) system, methods and techniques (as described in publications 13 and 14 identified below) has been developed. Certain accurate OCT diagnostic criteria have been developed for specialized intestinal metaplasia, dysplasia and adenocarcinoma, as described in International Patent Application PCT/US2004/029148, filed Sep. 8, 2004, U.S. patent application Ser. No. 10/501,276, filed Jul. 9, 2004, and publications 15-17 identified below. For example, advances in OCT technology have occurred demonstrating that the acquisition of an OCT signal in the wavelength domain (as opposed to the time domain) can provide orders of magnitude improvement in imaging speed while maintaining excellent image quality, as described in publications 18-20 identified below. One such exemplary second-generation imaging technology has been developed, e.g., optical frequency domain imaging (OFDI), as described in U.S. patent application Ser. No. 11/266,779, filed Nov. 2, 2005 and publication 21 identified below. With OFDI methods, techniques and systems, high-resolution ranging can be conducted in a tissue by detecting spectrally-resolved interference between the tissue sample and a reference while the source wavelength is tuned. (See, e.g., publication 22 identified below). Currently, OFDI methods, techniques and systems may be capable of capturing (e.g., 10 µm) 3 voxels at rates of approximately 40 million per second and the imaging speeds may likely be more than double in the near future, as provided in publication 23 identified below. Additionally, phase-sensitive OFDI methods, techniques and systems has been used for imaging flow, as provided in publication 24 identified below.

Controllable Therapy

Certain endoluminal approaches have been evaluated for the treatment of SIM (with and without dysplasia), including photodynamic therapy (PDT) (as provided in reference 25 identified below), laser (532 nm and 1064 nm) (as provided in reference 26 identified below), multipolar electrocoagulation (as provided in reference 27 identified below), argon plasma coagulation (as provided in reference 28 identified below), endoscopic mucosal resection (as provided in reference 29 identified below), radiofrequency ablation (as provided in reference 30 identified below) and cryoablation (as provided in reference 31 identified below) using liquid nitrogen. Although each of these techniques appear to be successful, most studies describe non-uniform therapy that can potentially result in persistent SIM or excessively deep ablation, resulting in stricture or perforation. In a study of over 100 patients, PDT may result in a stricture rate of 30% for single treatments and 50% for more than one treatment (as provided in reference 32 identified below). An exemplary reason for failure is not entirely clear but possible contributing causes include the operator-dependent nature of many of these hand-held, hand-aimed devices, the large surface area that requires treatment and the inherent preference for a physician-determined visual end point for the treatment (as provided in references 3 and 30 identified below). Additionally, a high variability may exist in the thickness of mucosal layers within and between patients and have directly observed significant compression of the soft tissues of the esophagus. The prior therapeutic approaches, however, do not account for the variability of layer thickness or compressibility of the esophageal wall.

Accordingly, there is a need to overcome the deficiencies described herein above.

OBJECTS AND SUMMARY OF THE INVENTION

To address and/or overcome the above-described problems and/or deficiencies as well as other deficiencies, exemplary embodiments of methods and systems can be provided for monitoring at least one portion of a sample using conformal laser therapy procedures, providing electromagnetic radiation thereto and obtaining information associated with at least one characteristic of the sample.

Such deficiencies can be addressed using the exemplary embodiments of the present invention. In one exemplary embodiment of the present invention, a method and system are provided for obtaining information associated with at least one portion of a sample. For example, a temperature change can be caused in the portion of the sample. At least one first electro-magnetic radiation can be forwarded to a section near or in the portion of the sample. A deformation of the section can be identified at a plurality of depths as a function of (i) a phase of at least one second electro-magnetic radiation provided from the section, and/or (ii) a rate of change of the phase and/or an amplitude of the second electro-magnetic radiation.

It is possible to generate an interferometric signal associated with the second electro-magnetic radiation, and determine the phase of the second electro-magnetic radiation using the interferometric signal. The interferometric signal can be measured as a function of a wavelength of the second electro-magnetic radiation. The first electro-magnetic radiation can have a wavelength that varies over time. The temperature change may be caused using a laser arrangement. A border can be defined between the at least one changed portion and an unchanged portion of the sample as a function of the information associated with the deformation. The sample can be a biological structure, and the changed portion may be denatured, damaged and/or destroyed. In addition, an interferometric signal associated with the second electro-magnetic radiation can be generated, and the amplitude of the second electro-magnetic radiation can be determined using the interferometric signal. The interferometric signal can be measured as a function of a wavelength of the second electro-magnetic radiation.

In another exemplary embodiment of the present invention, a method and system are provided for controlling a temperature distribution in a sample. For example, an electro-magnetic radiation can be provided to the section in the sample at a particular wavelength. The temperature distribution can be controlled by modifying the particular wavelength of the electro-magnetic radiation when the electro-magnetic radiation is provided to the section.

In particular, the modification to the particular wavelength can change a distribution of damage in at least one portion of the sample. The temperature distribution can be further controlled by modifying a power of the electro-magnetic radiation. The particular wavelength may be modified to be in a range of approximately (i) about 1.35 µm to 1.5 µm and/or (ii) about 1.7 µm to 2.2 µm. The temperature distribution can be substantially due to an absorption of the electro-magnetic radiation by water. The electro-magnetic radiation can be provided by a thulium laser amplifier arrangement and/or an erbium laser amplifier arrangement. A rate at which the particular wavelength is modified can be greater that about 10 nm per second. The particular wavelength may be modified in a non-random manner.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which.

Figure 1A:
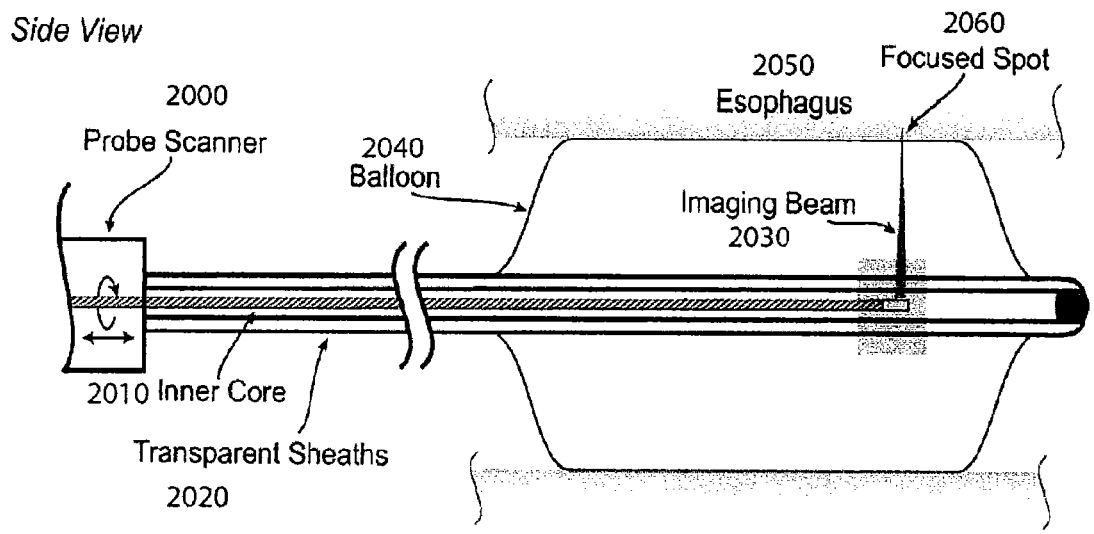
FIG. 1A is a schematic diagram of an OFDI balloon catheter in accordance with an exemplary embodiment of the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

An exemplary embodiment of the system and method according to the present invention for controlling and localizing therapy can be based on a thermal excitation delivered by a conventional, spatially scanned laser beam. For example, in the absence of photochemical or phase transition processes, the laser energy absorbed by tissue can be substantially or entirely converted to a temperature rise, as described in publication 33 identified below. For exposure durations greater than approximately 10 ms, temperatures in excess of 60-70° C. generally can lead to irreversible protein denaturation and cell death irrespective of duration, as described in publication 34 identified below. When the energy is absorbed, it can be subject to a spatial redistribution by a thermal diffusion. In 1983, as described in publication 35 identified below, an exemplary concept was described which provided that spatially confined microsurgical effects (selective photothermolysis) can be achieved by the use of laser exposures that are shorter than the characteristic thermal diffusion time of the heated volume. For a relatively large (>1 mm) diameter laser beam and laser wavelengths in the vicinity of 1450 nm, this characteristic diffusion time for biological tissues may be on the order of 1 second. Under these conditions, the temperature increase can be determined by the laser power density, $P_d$, the absorption coefficient, μa, and the duration of exposure t (as described in publications 33 and 34 identified below) as follows:

$$\Delta T(t, r, z) \approx \frac{P_d t \mu_a}{\rho c} \exp\left(-\mu_a z - \frac{2r^2}{W^2}\right) \qquad \text{Eq. 1}$$

where ρ is the tissue density, c the heat capacity, and r the radial distance from the center of a Gaussian laser beam of 1/e2 radius, W. Although this approximation neglects scattering of the laser light as it propagates into the tissue, models that explicitly include scattering (as described in publication 36 identified below) indicate less than 10% deviation from Eq. 1 under the stated conditions.

Since the absorption coefficient is wavelength-dependent, Eq. 1 indicates that laser parameters $P_d$, t, and wavelength can be used to control the depth of thermal injury and to minimize collateral damage to underlying tissues. Operating in the visible portion of the spectrum is challenging since absorption is governed by a wide range of chromophores whose concentration is highly variable across different tissues and pathologic conditions. By comparison, the absorption spectrum of biological tissues near 1.45 μm may be dominated by water, and can therefore be roughly constant across a range of tissues. Additionally, by tuning over a modest wavelength range, from 1375 nm to 1430 nm for example, absorption lengths can be selected that range from over 2 mm to 300 μm. This exemplary range is well matched to the depths characteristic of epithelial lesions.

Exemplary Monitoring

Several approaches have been investigated for monitoring laser therapy, including the analysis of the acoustic transients generated during ablation (as described in publication 37 identified below), changes in tissue reflectivity (as described in publications 38 and 39 identified below), fluorescence spectroscopy for discrimination between plaque and vessel wall (as described in publication 40 identified below), plasma spectroscopy to distinguish between bone and nerve tissue (as described in publication 41 identified below), and analysis of the cavitation bubble dynamics at the tip of a laser optical probe for controlled sclera perforation in glaucoma surgery (as described in publication 42 identified below). With the exception of the procedures that are based on a reflectivity described in publications 38 and 39, in each of such methods, the monitoring signal arose only after the zone of thermal injury has transitioned across a boundary of the specific tissue types. None could determine the depth of thermal injury or the spatial relationship of the damaged tissue to adjacent viable tissue. Certain degree of spatial resolution has been achieved by monitoring the portion of laser light that is not absorbed by the tissue. By inserting an optical fiber through a needle, this light can be collected from different perspectives surrounding the heated volume and temperature-dependent scattering changes can be measured (as described in publication 43 identified below). A more direct approach, high-resolution in situ imaging, has also been demonstrated for visualizing scattering changes and the physical removal of tissue resulting from ablative laser irradiation (as described in publication 44 identified below).

Exemplary embodiments of monitoring systems, methods and techniques according to the present invention may utilize information regarding well-known tissue responses to a thermal injury. These exemplary responses can include, but not limited to, microscopic deformation (as described in publication 33 identified below) and changes in scattering (as described in publications 36, 38 and 45 identified below), birefringence (as described in publication 46 identified below), and blood flow (as described in publication 47 identified below) that can result from laser heating and that can be observed over a range of temperatures beginning as low as 45° C. One exemplary aspect of an exemplary embodiment of the method and technique according to the present invention is that these thermal responses can be detected with high spatial resolution and presented in a cross-sectional image format along with the microscopic tissue structure.

Exemplary Strategies for Conformal Laser Therapy

According to an exemplary embodiment of the present invention, a system, arrangement and method can be provided that are capable of screening and delivering precisely guided laser therapy. Since the characteristic length-scales preferably usable for comprehensive screening and comprehensive therapy are likely distinct, it is possible to separately perform these objectives. For example, the screening (e.g., possibly performed as a first step) may utilize comprehensive imaging technique(s) with a resolution on the cellular size-scale. This exemplary procedure can be used to identify regions for subsequent therapy. After the performance of the screening procedure, the endoscopic probe can be directed back to the specified regions, and therapy may be performed under real-time guidance so that all disease is treated and collateral damage is minimized. This exemplary result can improve the management of patients with Barrett's esophagus by, e.g., increasing the effectiveness of therapy while decreasing the risk of complications.

Although described in conjunction with a treatment of epithelial cancers, the exemplary embodiments of the system, techniques and methods according to the present invention can be applicable to any application of laser treatment including but not limited to, for example, applications in dermatology. Some relevant epithelial cancers and precancerous lesions addressed by the exemplary embodiments of the present invention can include, but not limited to, the larynx, cervix and ovaries, bladder, oral cavity and lung. In addition, the exemplary embodiments of the present invention can be applicable to the areas of monitoring photodynamic therapy, radiofrequency ablation, and cryotherapy to provide control over depth and spatial extent of therapy.

Exemplary Wide-Field Screening

In order to perform an effective screening procedure, it is preferable to conduct a comprehensive examination of large surface areas and the application of accurate diagnostic criteria in order to identify specific regions of pathology. Various OCT diagnostic criteria has been developed and verified for specialized intestinal metaplasia, dysplasia and adenocarcinoma, as described in publications 15-17 identified below. For example, across 288 biopsies obtained from 121 patients, a sensitivity and specificity for diagnosing SIM (versus all other upper GI tract tissues) has been determined of about 97% and 92%, respectively, as described in publication 16 identified below. Until recently, however, the exemplary OCT technique was too slow to image large mucosal surface areas. As discussed herein below, advances have been made that may overcome this timing issue, and provide a preliminary demonstration of comprehensive esophageal imaging in vivo.

Optical Frequency-Domain Imaging (OFDI)

As described above, publication 21 identified below describes the development of the OFDI technique as an alternative to the use of the OCT techniques. Although the light source (as discussed in publication 22 and 23 identified below) and the detection principles of OFDI are useful, the contrast, resolution and cross-sectional image presentation are approximately equivalent or similar to those provided by OCT. One of the advantages of OFDI is that OFDI has a higher detection sensitivity, thus enabling a significant increase in the image acquisition speed, without compromising image quality. The system used for these preliminary studies was designed specifically for endoscopic imaging and provides an acquisition rate of 10,000 depth-scans (A-lines) per second, an axial resolution of 8 μm in tissue, and a ranging depth of 3.5 mm, as described in publication 24 identified below. The imaging speed of this exemplary system is limited solely by the rate at with which data can be transferred across the computer's bus and stored to a hard drive.

Exemplary Balloon Catheter

Figure 1B:
FIG. 1B is a photograph of the OFDI balloon catheter shown in FIG. 1A.

For comprehensive esophageal imaging, an exemplary embodiment of an OFDI catheter may be provided in accordance with the present invention that can be centered within the esophageal lumen using a balloon sheath shown in FIGS. 1A and 1B. The exemplary catheter may include of a probe scanner 2000 which can rotate, and may pull back an inner optical core 2010. The inner core 2010 can be enclosed within a transparent sheath 2020. At the distal end of the catheter, the balloon 2040 which, when inflated, may center the imaging optics. The imaging beam 2030 can be focused onto the esophageal surface 2050. This imaging beam 2030 may be scanned to achieve comprehensive imaging. The balloon 2040 can have an inflated diameter of 1.8 cm, and may allow for a longitudinal imaging over a length of 4.5 cm without repositioning. The optical core 2010 of the catheter can include an optical fiber, a spacer for expansion of the optical beam, a gradient index lens for focusing, and a right-angle prism for directing the beam perpendicularly to the longitudinal axis of the catheter. A miniature cylindrical lens was fabricated in-house and placed on the second surface of the prism. This lens compensated for astigmatism induced by the plastic sheaths and resulted in a diffraction-limited beam (30 μm diameter) on the tissue surface. In use, the exemplary catheter may be rotated at rate of about 4 revolutions per second, allowing the acquisition of 2500 axial scans per circular cross-section. This exemplary OFDI system can record an encoder signal to precisely track the rotation and pull-back of the catheter. This information is used in reconstructing the 3-dimensional data set.

Preliminary Porcine Esophageal Imaging

Figure 2:
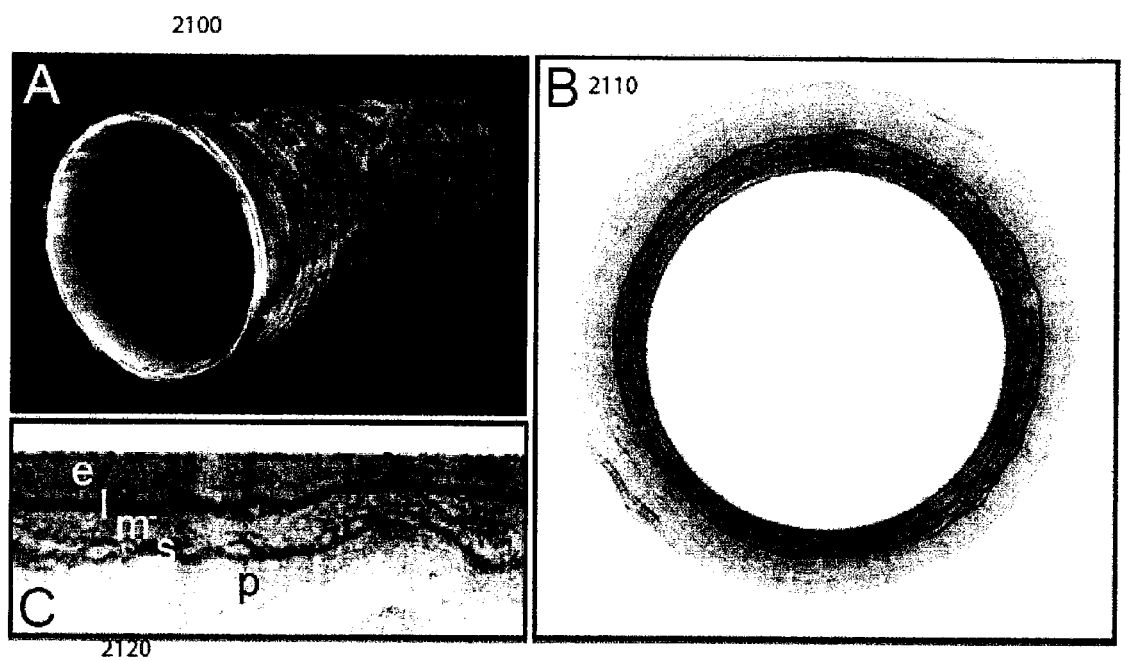
FIG. 2A is an exemplary image of a perspective view of a swine esophagus obtained using the OFDI balloon catheter in accordance with an exemplary embodiment of the present invention.
FIG. 2B is an exemplary image of a top view of the swine esophagus of FIG. 2A.
FIG. 2C is an exemplary image of a side view of a wall of the swine esophagus of FIG. 2A.

The esophageal imaging techniques can be performed in two ~50 kg swine. Although the complete 20 GB data set may likely not be represented in discrete figures, the information content is shown by FIGS. 2A-2C. For example, in a perspective view of FIG. 2A, an image 2100 provides a 3D rendering of the entire imaged esophagus. In a front view of FIG. 2B, an image 2110 illustrates a single transverse cross section of the imaged esophagus. In FIG. 2C, image 2120 shows a zoomed cross sectional image of at least one portion of the esophagus. A sampling with a resolution of 10 μm×20 μm×30 μm (r,θ,z) can yield a comprehensive microscopic data set that can be displayed volumetrically a the image 2100 of FIG. 2A for mapping and orientation, or in high-resolution cross-sectional images in which the entire esophageal wall can be visualized as the image 2110 in FIG. 2B. An expanded view of the image 2120 of FIG. 2C depicts the architectural structure of the mucosal layers.

Preliminary Human Esophageal Imaging

Figure 3:
FIG. 3 is an exemplary OFDI image acquired in a human subject using a BE technique in accordance with an exemplary embodiment of the present invention.

An exemplary single rotational image 2150 is shown in FIG. 3. Hallmark features of SIM (disorganized epithelial architecture with irregular surface; presence of large epithelial glands) of a patient are shown therein. This patient had a prior diagnosis of BE, and imaging was performed prior to PDT.

These preliminary studies demonstrate that a) comprehensive OFDI microscopic imaging in vivo is feasible, b) the architectural structure of the entire esophageal wall can be visualized, and c) features important to the diagnosis of SIM in human subjects can be detected using the balloon centering probe.

Monitoring Laser Thermal Injury

In response to heating, tissue proteins and collagen can denature, giving rise to microscopic deformation (described in publications 33 identified below), increased in scattering (described in publications 36, 38 and 45 identified below), reduced birefringence (described in publication 46 identified below), and reduced blood flow (described in publication 47 identified below). The description below provides the methods for monitoring these changes using exemplary OFDI in accordance with the exemplary embodiments of the present invention. In the exemplary demonstration of each, freshly obtained porcine esophagus samples and duodenum samples (as a proxy for SIM) were mounted with a microscope cover glass on the epithelial surface so that the approximate pressure and thermal conductivity of the balloon catheter could be simulated.

Figure 4:
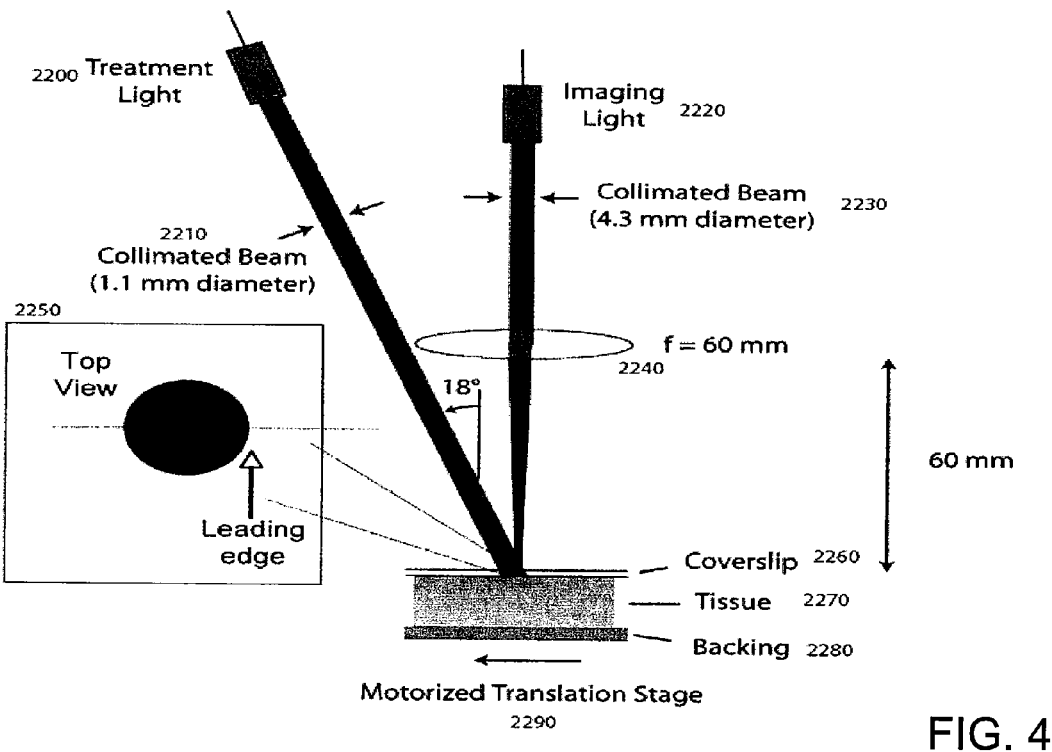
FIG. 4 is a schematic diagram of exemplary arrangement and usage thereof for treating and monitoring tissue in accordance with an exemplary embodiment of the present invention.

An exemplary embodiment of an apparatus for collecting OFDI signals during a laser irradiation and use thereof according to the present invention is shown in FIG. 4. For example, the treatment light is delivered through a collimator 2200. The imaging light is delivered through a second collimator 2220. The treatment beam 2210 and imaging beam 2230 overlap when reaching the tissue 2270 which is covered with a think glass cover slip 2260 and resting on a backing 2280. The tissue is translated by a motorized translation stage 2290. The imaging beam is focused by a lens 2250. The top-down image depicting beam overlap 2250 is provided. For a thermal excitation, a collimated, high-power Gaussian laser beam (e.g., diameter=1.1 mm; wavelength=1450 nm; power=400 mW) can be used. The OFDI sampling beam can be focused at the tissue surface to, e.g., a $1/e^2$ intensity diameter of 23 μm and aligned so that it overlapped with the laser spot as shown in FIG. 4. During the data collection, the samples may be held at a fixed location and/or translated using a motorized stage.

Exemplary Microscopic Deformation

As laser energy is deposited in tissue, the resulting temperature increase can denature proteins and collagen. These changes can be manifested by microscopic deformation that can be measured using phase-sensitive OFDI. The following data demonstrates this capability.

Figure 5:
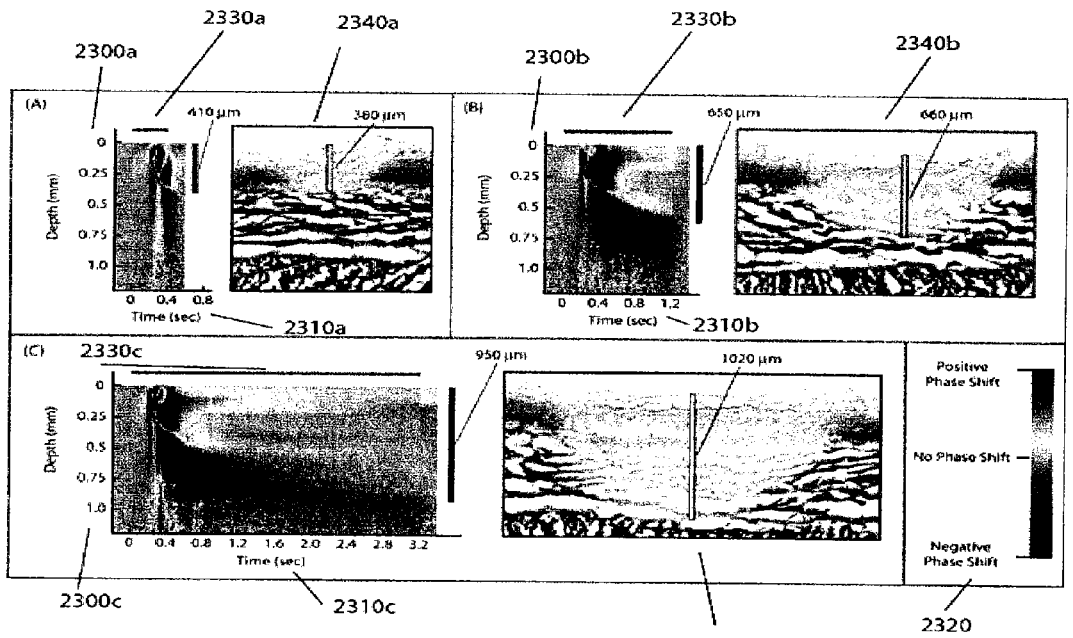
FIG. 5 is a set of multiple exemplary m-mode OFDI phase images obtained using the exemplary arrangement of FIG. 4 together with a corresponding histology.

Fixed spot—For such exemplary experiment, the samples were held at a fixed location. OFDI depth-scans were acquired continuously at a rate of about 10 kHz while the 1450 nm laser was switched on, held at a constant power of 400 mW for a predetermined duration, and switched off. Representative data for three different laser exposure durations is shown in the graphs of FIG. 5 as "M-mode" images where the vertical axis 2300*a*, 2300*b*, 2300*c* represents depth within the tissue, the horizontal axis 2310*a*, 2310*b*, 2310*c* denotes time and the magnitude of the measured phase-shift is represented using a color lookup table 2320 (red=positive phase-shift; blue=negative). A red horizontal line 2330a, 2330b, 2330c, at the top of each phase-shift image denotes the interval over which the laser was on. Upon initial laser exposure, a superficial region of positive phase-shift overlying a lower region of negative shift has been observed. As the laser irradiation continued, the depth at which the phase transitioned from positive to negative became progressively deeper and the magnitude of the overlying phase-shift decreased. No measurable phase-shift was detected after the laser was switched off. A protein denaturation gives rise to local microscopic structural changes and a nidus of local deformation that is detected as a phase-shift in the interferometric signal. As the laser exposure continues, the zone of active denaturation propagates in depth with overlying tissues becoming completely denatured. The depth at which the direction of the phase-shift reverses identifies the focal center of active denaturation.

To verify these results, histological sections were obtained following laser exposure and nitro-blue tetrazolium chloride (NBTC) staining was used to assess the extent of laser damage. NBTC stains positive for lactate dehydrogenase (LDH), which is a thermolabile enzyme; loss of LDH activity ensues rapidly upon heat induced cell damage and is correlated with cell lethality (as described in publications 48 and 49 identified below). Therefore, the depth of the border between unstained and stained tissue have been selected as the depth of laser damage. Corresponding phase-shift data and histology are shown in 2340a, 2340b, 2340c. The preliminary findings suggest that the border between thermally denatured tissue and viable tissue corresponds with the inflection point of the phase-shift measured with OFDI. Quantitatively, the depth-derivative of the phase-shift has been determined for each A-line and defined the depth of injury as the point of maximum negative value of the derivative. The depths determined in this way are provided in FIG. 5 as vertical lines adjacent to each M-mode image and show a good correspondence with histomorphometry.

Translating spot—Laser treatment of large epithelial surface areas can be facilitated by adding a therapeutic laser beam to the existing OFDI catheter so that the laser and OFDI beams are simultaneously scanned. The preliminary imaging studies demonstrated comprehensive esophageal imaging with an OFDI beam size of 30 μm. Obtaining a precise alignment of >1 mm diameter laser beam on successive rotational scans should therefore be obtainable. To simulate the monitoring while scanning, the computer-controlled translation stage 2290 (see FIG. 4) can be controlled to repetitively toggle the sample velocity from 1.8 mm/s to 0.9 mm/s.

Figure 6:
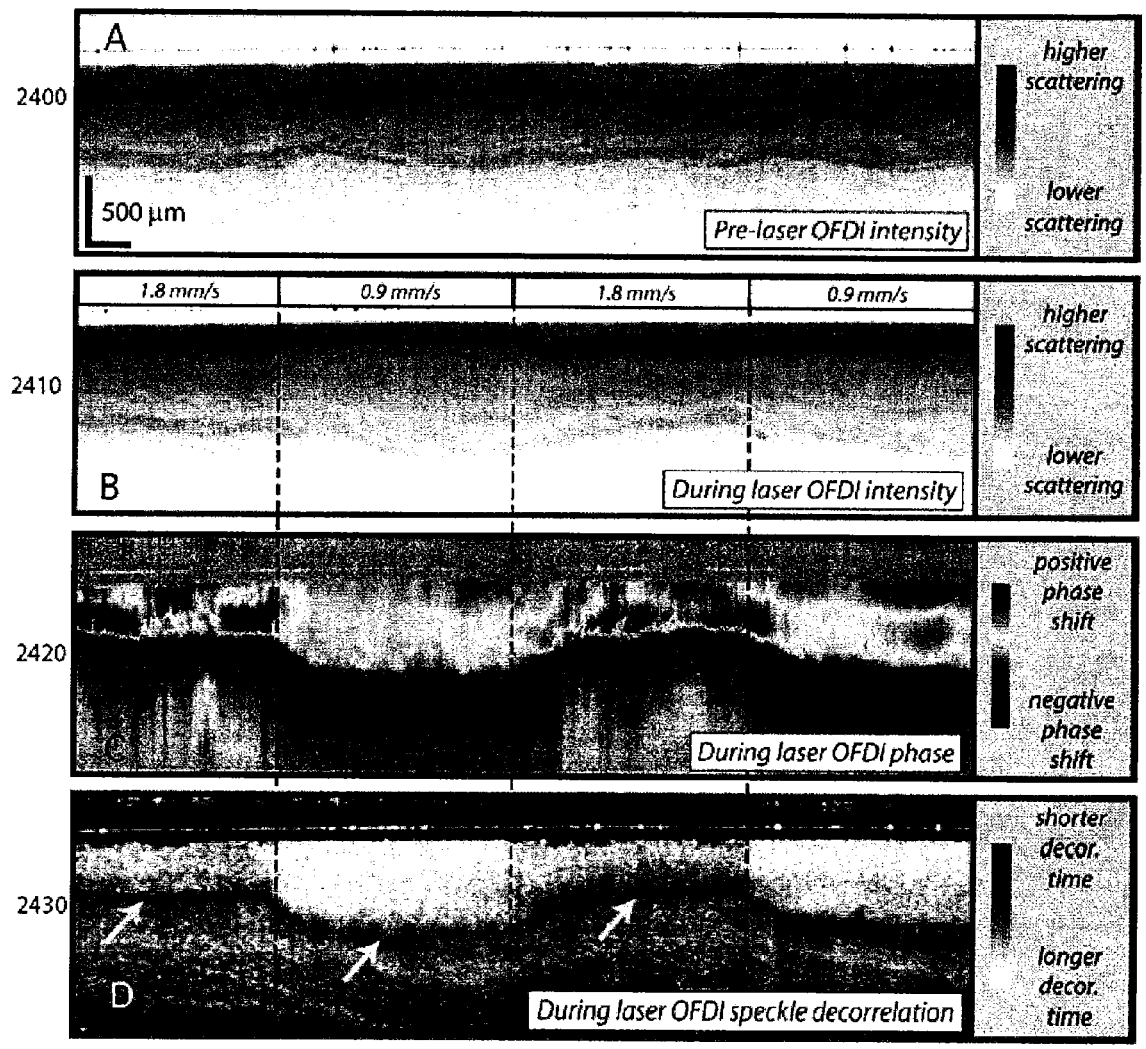
FIGS. 6A-6D are exemplary images associated with the OFDI data acquired for a translating sample in accordance with the exemplary embodiment of the present invention.

An OFDI intensity image 2400 acquired with no laser irradiation is shown in FIG. 6A. For the images 2410, 2420 and 2430 shown in FIGS. 6B, 6C, and 6D, respectively, the 1450 nm laser power was about 400 mW. The translation of the samples during the exposure resulted in a line of laser damage across the surface of the sample. Since the thermal energy deposition can be proportional to the exposure time (see Eq. 1), the depth of laser damage can vary along the line according to the inverse of the translation velocity. Histology sections, obtained from regions of fast and slow translation and with an orientation perpendicular to the line, indicated laser injury depths of 0.41 mm and 0.69 mm respectively. The phase-shift data corresponding to the image 2410 of FIG. 6B is illustrated as the image 2420 in FIG. 6C. In a substantial agreement with the histomorphometric measurements, the depth of the damage determined by the phase-shift data (max negative derivative) can be 0.40 mm and 0.67 mm in the regions of fast and slow velocity, respectively.

Speckle Decorrelation

Speckle is a phenomenon that is commonly observed when imaging with coherent illumination and manifests as a grainy pattern of high- and low-intensity that does not appear to correlate with the macroscopic structure. In tissue, speckle generally arises from the interference between photons that have traversed different paths during propagation within the sample. If the scatterers within the tissue are moving, even on a microscopic scale, the speckle pattern is likely seen to rapidly fluctuate. The measurements of the time-evolution of the speckle pattern can therefore provide insight into microscopic motion within the sample. This exemplary technique has been provided for investigating biomechanical properties (as described in publication 50 identified below), and thermal excitation (as described in publication 51 identified below), in biological tissues. The extension of these concepts to the depth-resolved monitoring of laser tissue interactions with OFDI has been reviewed.

Viewing the OFDI images of the tissue during laser exposure provides an indication of the potential of this exemplary technique. With no laser exposure, the speckle pattern observed in OFDI remained constant over the depth and transverse extent of the image. Under laser irradiation, the speckle pattern was observed to rapidly fluctuate in the local region of the laser beam. In slow-motion viewing, we observed that the speckle fluctuations began near the tissue surface and propagated downward in time. To quantify these observations, the rate of speckle decorrelation for each depth point of the image 2410 shown in FIG. 6B has been determined. In particular, the depth-dependent width of the temporal autocorrelation function of the OFDI intensity signal has been determined. Speckle decorrelation images were then generated by displaying the autocorrelation width using a grayscale lookup table. The image 2430 of FIG. 6D is the speckle decorrelation image corresponding to the images 2410 and 2420 of FIGS. 6B and 6C, respectively. The depth of the peak decorrelation 2431 rate (black band, denoted by arrows in FIG. 6D) can be observed to vary in correspondence with the translational rate of the sample and the depth of laser damage indicated in histology. The consistency of this finding across samples of esophagus and duodenum confirm that the depth of peak decorrelation rate is a quantifiable metric for determining the depth of laser injury.

Birefringence

As light propagates within materials, its polarization state can become altered if the index of refraction is non-isotropic. This effect is known as birefringence. Many tissues, especially muscle and collagen, exhibit strong birefringence which is lost upon thermal heating and denaturation (as described in publication 46). Polarization-sensitive OCT (PS-OCT) techniques, methods and systems have been described for quantifying burn depth through measurements of birefringence loss. (See publications 52 and 53 identified below). In PS-OCT, two detector channels can be configured to receive orthogonal polarization states of the light returning from the sample. Birefringent samples induce a depth-dependent rotation of the polarization state, resulting in a variation in the percentage of the sample light detected in each channel. If the ratio of the two channels is displayed as a grayscale in a cross-sectional image, birefringence is observed as a characteristic banding pattern.

Figure 27:
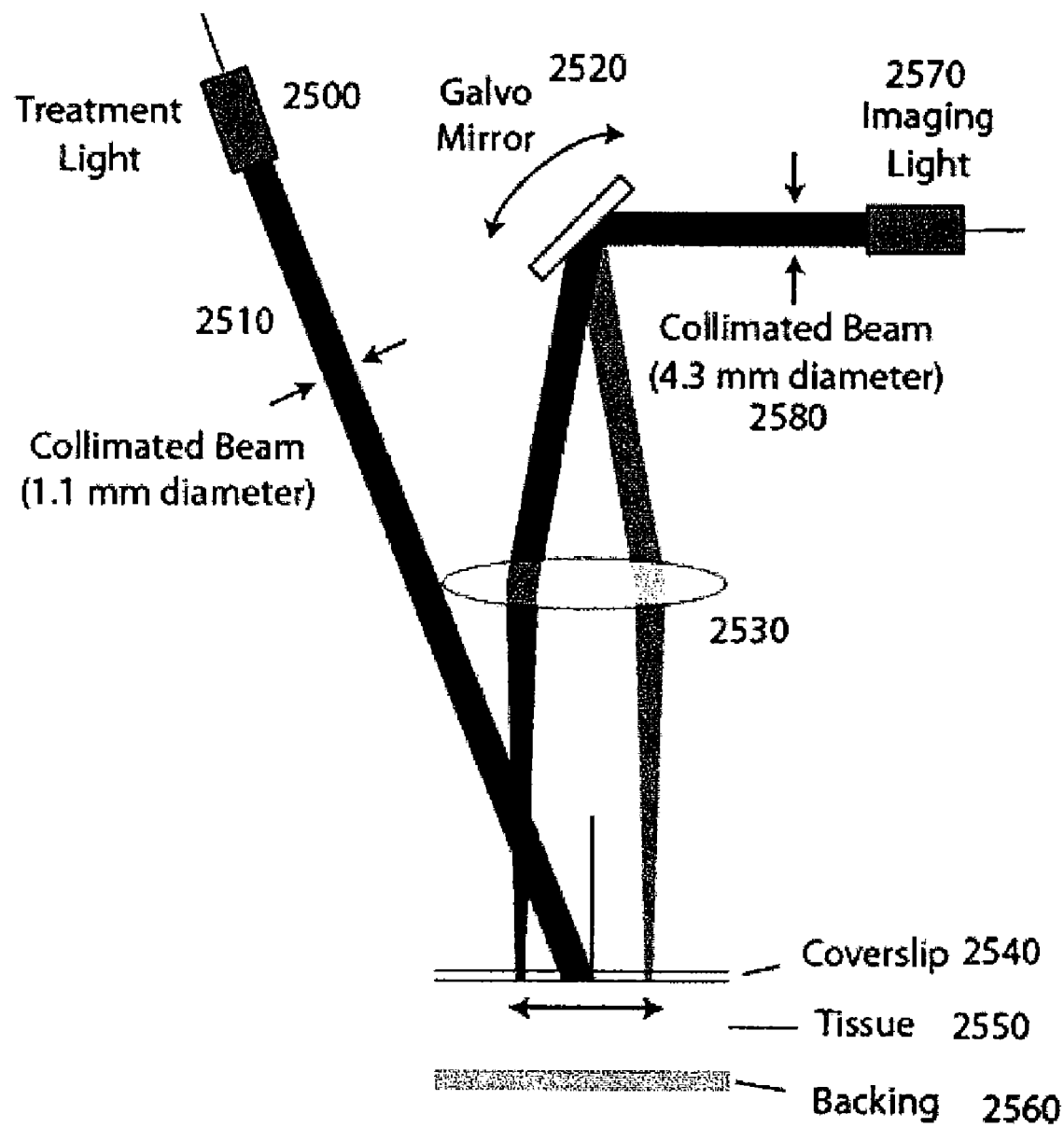
FIG. 27 is a side view of another exemplary embodiment of a system which includes a galvanometric scanner which can allow the OFDI beam to be repetitively scanned across the surface of the tissue, and usage thereof.

For example, the apparatus of FIG. 4 can be modified to include a galvanometric scanner so that the OFDI beam may be repetitively scanned across the surface of the tissue while the sample was held stationary and the 1450 nm laser spot remained fixed on center, as shown in FIG. 27. As shown in FIG. 27, the treatment light can be delivered through a first collimator 2500 providing a treatment beam 2510 incident on the tissue 2550 that is covered by a cover slip 2540 and against a backing 2560. The imaging light may be provided by a second collimator 2570 producing an imaging beam 2580 that is directed by a galvo-mirror 2520 through a lens 2530. This arrangement/system can be an exemplary embodiment of a therapeutic monitoring system applicable to applications in dermatology. OFDI images or video of esophageal and duodenal tissues were acquired during laser irradiation.

FIGS. 7A-7D show images of the representative data. In frames acquired prior to laser irradiation, the layered esophageal structure can be observed in the intensity image 2450 (see FIG. 7A) and characteristic birefringence banding can be observed in the corresponding polarization image 2460 (see FIG. 7B). In frames acquired during laser exposure, the epithelial scattering intensity may be increased dramatically within the 1.1 mm laser spot 2470 (see FIG. 7C), and the birefringence banding in the corresponding polarization image 2480 (see FIG. 7D) can be lost. Reviewing the polarization moving images in slow-motion, a zone of decreased birefringence can be observed that may begin near the surface and propagated downward. These observations are generally consistent with a downward propagating zone of denatured tissue. Measurements of the percent-loss of birefringence is a quantitative metric for monitoring laser thermal damage.

Scattering

Thermally induced changes to the microscopic structure of tissue can alter optical scattering. Since the signal in OFDI arises from scattering and small changes can be detected over a large dynamic range, we investigated the use of scattering measurements for monitoring thermally induced changes in tissue. Scattering changes observed in image 2460 of FIG. 7B may be representative of the preliminary observations in both duodenum and esophagus samples. In certain cases, it was determined that the significant scattering changes within the epithelium and relatively smaller changes in the underlying tissues of the muscularis mucosa and muscularis propria. For example, two potential quantitative metrics for laser damage that could be obtained from scattering measurements: changes in the depth-resolved scattering intensity and changes in the depth-integrated scatting intensity.

Blood Flow

Figure 8:
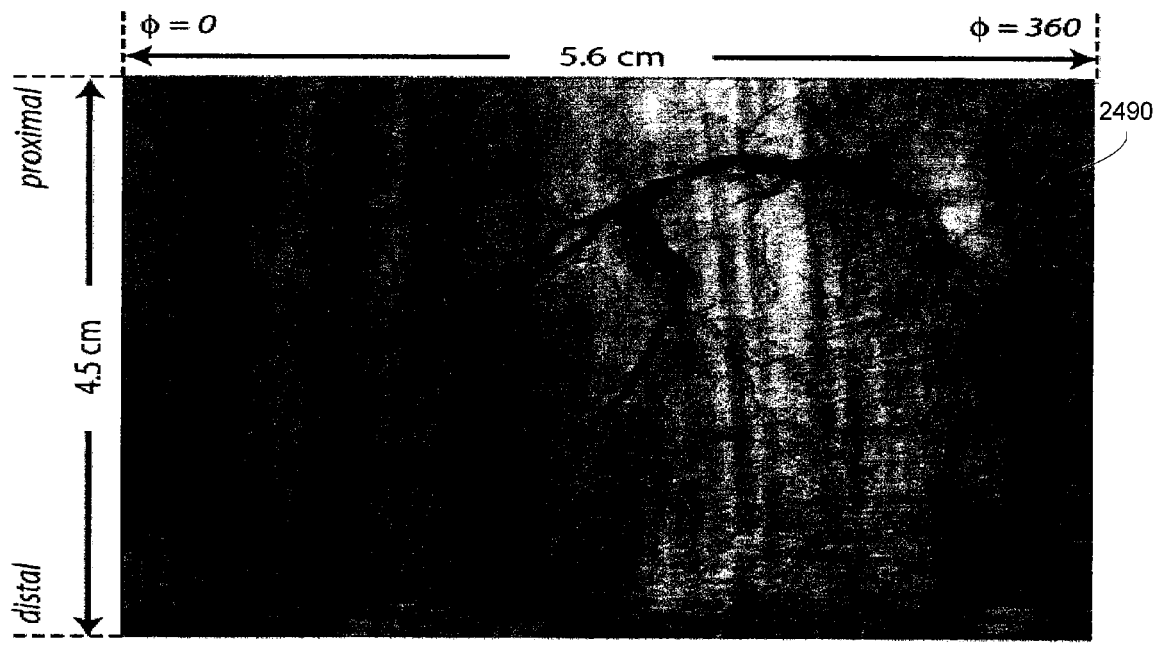
FIG. 8 is an image of an exemplary vascular map extrated from a comprehensive dataset obtained from porcine esophagus in-vivo which can be obtained using the exemplary embodiment of the present invention.

Laser therapy can to alter vessels and capillaries resulting in decreased blood flow (as described in publication 54 identified below). Since the esophageal mucosa is highly vascularized, monitoring changes in blood flow may provide an additional method for monitoring laser therapy. An image 2490 of FIG. 8, acquired during our recent swine studies, graphically illustrates the porcine esophageal vascularity. This exemplary image 2490 was generated by unwrapping the tubular image data to display the epithelial surface as if the esophagus was longitudinally opened and pinned flat. The intensity data has been integrated over depth into the tissue. Although this type of large scale visualization is a convenient way to map the vessels, it is possible to use a more sensitive and quantitative method/technique/system for measuring blood flow. Doppler OCT (as described in publications 55 and 56 identified below) has been demonstrated for visualizing and quantifying blood flow in tissue and has been investigated as an arrangement for assessing flow following laser therapy (as described in publication 57 identified below). The Doppler measurements with OFDI (as described in publication 24 identified below) have been described, and the possibility of simultaneously measuring structure and flow in vivo has been reviewed.

Figure 9:
FIG. 9 is an exemplary in-vivo Doppler flow image of a porcine esophagus obtained using the exemplary embodiment of the present invention.

A cross-sectional view of an exemplary image 2590 of FIG. 9 has been acquired in the esophagus of a living swine and displays intensity as a grayscale and Doppler as a superimposed color. The coordinates $(r,\theta)$ of this data have been mapped to Cartesian coordinates (vertical, horizontal) for simplicity of display. This result was representative of our observations at multiple locations in two swine. Additionally, in time-sequences of Doppler images, we clearly observed pulsatile flow.

| Summary of Monitoring | | |
|---|---|---|
| Cause | Effect | Measurement |
| Thermal denaturing of cellular proteins and collagen | Focal deformation Loss of birefringence Δ Scattering | Phase &Speckle Polarization Intensity |
| Thermal coagulation of vessels | Loss of blood flow | Doppler flow & Vascular Map |

Based on the preliminary investigation, the proposed measurements would likely be complementary: and the phase-shift and speckle decorrelation, which are only applicable during laser irradiation, may be more sensitive and provide greater spatial resolution. The changes in birefringence, scattering and flow are persistent and could be applied for follow-up imaging after laser treatment.

Exemplary Control

In addition to monitoring for laser thermal injury, effective conformal laser therapy may use precise control over the volume of treated tissue. One exemplary approach to controlling treatment depth is to operate within the conditions for thermal confinement in order to minimize collateral damage and to manipulate laser wavelength, power, and exposure time to control the depth of thermal injury. In the transverse dimension (along the epithelial surface), thermal injury can be controlled through the use of a raster-scanned, spatially-collimated beam. A flat-top beam with a diameter of 1-3 mm with well-defined edges may allow spatial control while also permitting therapy of large epithelial areas through raster scanning. Exemplary laser control parameters are described herein below in the context of Eq. 1. The temperature distribution of Eq. 1 generally applies only in the limit of weak scattering.

Wavelength

Figure 10:
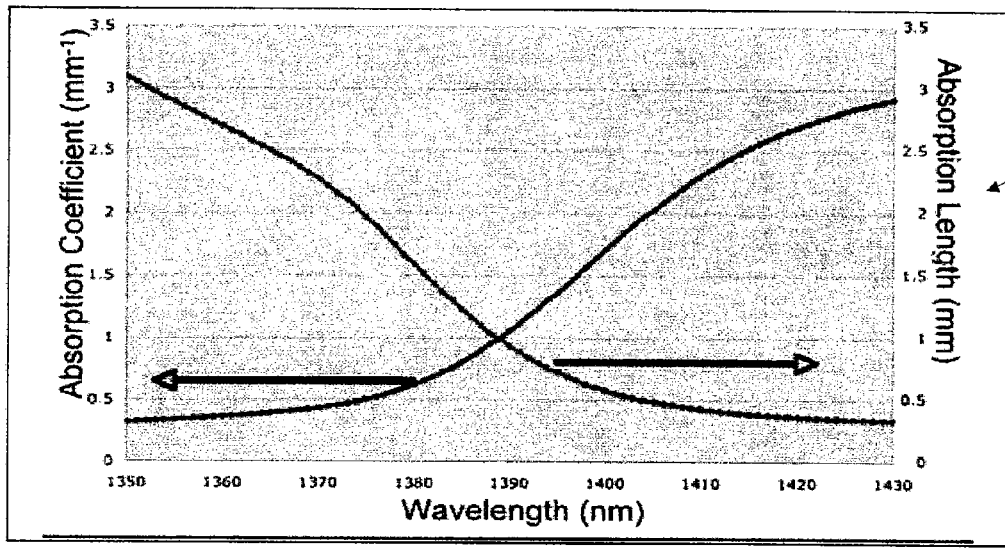
FIG. 10 is an plot of water absorption coefficient and corresponding penetration depth as a function of wavelength obtained using the exemplary embodiment of the present invention.

From the temperature distribution of Eq. 1, it is evident that $\mu_a$ would likely be an optimal parameter for control over depth of laser injury. Although $\mu_a$ is characteristic of the sample rather than an externally controllable parameter, in this invention we exploit the wavelength dependence of μa to achieve depth control. In this invention, we target the absorption coefficient at longer wavelengths where water absorption dominates. Since the water content is approximately constant in epithelial tissues, thermal injury depth can be closely regulated by changing the laser wavelength by small amounts. In the vicinity of the water absorption band near 1.45 μm, absorption lengths (see graph 2595 of FIG. 10) range from 0.3 mm to over 2 mm within a narrow spectral range (1375 nm to 1430 nm). These lengths correspond well to the characteristic length scales appropriate for the treatment of epithelial disease. A tunable laser, operable in the vicinity of the 1450 nm water absorption band can be used to control therapy through wavelength tuning.

Power and Exposure Duration

Upon the review of Eq. 1, the absorption coefficient does more than control the exponential depth decay of the temperature distribution; e.g., it also can control the amplitude. Since the amplitude term is also dependent upon power density and exposure duration, these variables can be used to normalize the amplitude while allowing the absorption coefficient to change.

Procedure Duration

In the evaluation of a proposed new therapy, it may be important to estimate the preferable procedure time and evaluate this estimate in the context of competing approaches and constraints specific to the clinical setting and patient acceptance. PDT is currently applied for the treatment of BE in the endoscopy setting and requires procedure times on the order of 20 minutes. For the exemplary conformal laser therapy technique, the procedure performance time may be estimated by $2At/(\pi rv)$, where At is the treatment area, r is the laser spot radius, and v is the laser spot scan velocity. For an esophageal treatment length of 60 mm and an esophageal diameter of 20 mm.

According to the exemplary embodiment of the present invention, a combined system can be provided which may allow for a controlled laser excitation. In one exemplary embodiment, the exemplary system can be used endoscopically for conformal laser therapy capable of comprehensively treating epithelial lesions while minimizing collateral damage to adjacent tissues.

Exemplary System Design

According to the exemplary embodiment of the present invention, a system can be provided for performing conformal laser therapy of epithelial disease through a combination of monitoring and control. Since laser beams can easily be shaped and spatially scanned and since margins in the transverse plane (along the surface of the esophagus) are less critical, the primary challenge for achieving accurate control of laser therapy is in limiting and adjusting the depth of laser damage. Based on the modeling and analysis described above, it is possible to utilize laser wavelength and power and scanning speed to vary the depth of laser damage over a clinically significant range while not significantly altering the transverse extent of injury.

Exemplary Therapy Laser Arrangement

The laser wavelengths between approximately 1375 nm and 1430 nm can provide absorption lengths ranging from over 2 mm to less than 0.3 mm. Semiconductor lasers can operate in this spectral range. Since such lasers can be compact and environmentally stable, these laser can be effectively used in clinical applications. Materials suitable for this specific wavelength range, however, may not be standard. A less expensive alternative for the early testing phase of exemplary embodiments of the methods according to the present can be provided by a solid-state laser material, tetravalent chromium-doped YAG (Cr4+:YAG). For example, a tunability with this material over the spectral range of 1340 nm-1570 nm can be implemented (as described in publications 58 and 59 identified below). The exemplary design and construction of tunable solid-state lasers that operate in the near infrared spectral range are described in publications 60-65 identified below. An electromechanical shutter, external to the laser resonator, can be used to turn on/off the exemplary laser.

Exemplary Benchtop System

An exemplary embodiment of a benchtop optical system according to the present invention may be provided that can be similar to the systems shown in FIGS. 4 and 27 and described herein. For example, the OFDI sampling beam may be focused at the sample to a diameter of ~25 μm. The axial location of the focus can be determined using a standard z-scan technique, and may be registered within the OFDI cross-sectional image. The subsequent axial positioning of the samples within the OFDI image window may ensure a constant focus location for all samples. Data may be collected with the two beams fixed with respect to each other and while the sample is translated perpendicular to the laser beam axis.

Exemplary Positioning and Registration of Laser and OFDI Beams

Figure 7:
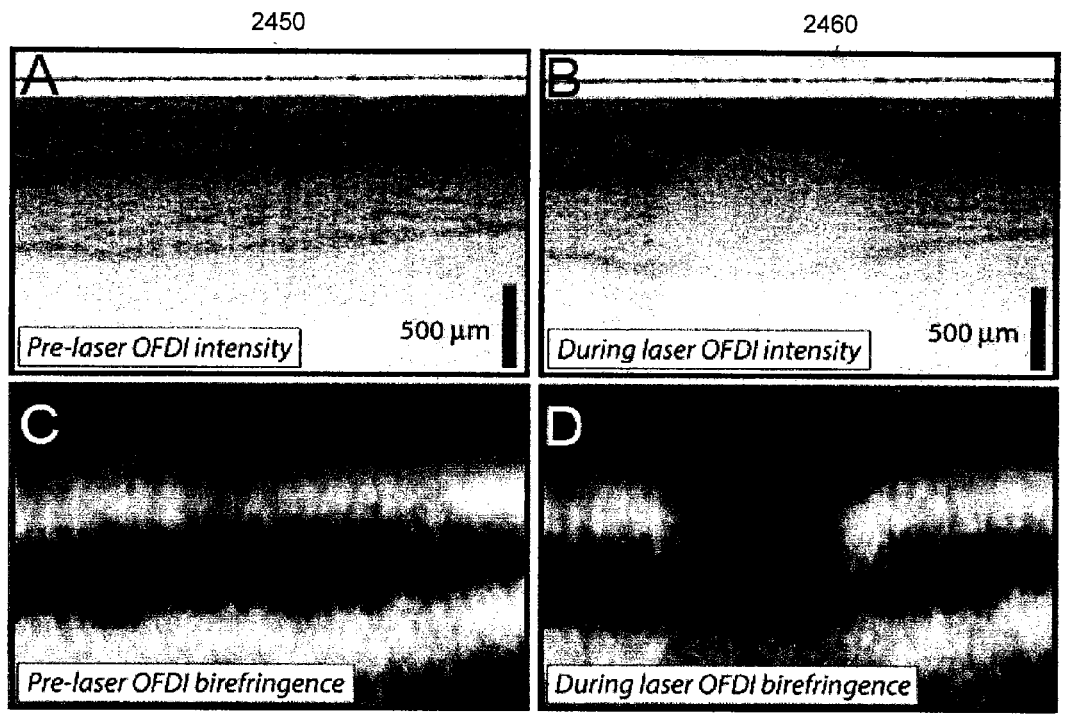
FIG. 7A is an exemplary pre-laser treatment OFDI image obtained using the exemplary embodiment of the present invention.
FIG. 7B is an exemplary pre-laser treatment birefringence image obtained using the exemplary embodiment of the present invention.
FIG. 7C is an exemplary post-laser treatment OFDI image obtained using the exemplary embodiment of the present invention.
FIG. 7D is an exemplary post-laser treatment birefringence image obtained using the exemplary embodiment of the present invention.

According to the exemplary embodiment of the present invention, the offset between the OFDI beam and the center of the laser spot is not critical for monitoring. OFDI data may be collected for various offsets (as depicted in FIG. 4) to determine the offset that yields the greatest indicated depth of thermal injury. This offset can then be used in all subsequent studies and may be registered as follows. A small, low-power, short-duration epithelial burn may be induced on the surface of the sample while the sample is held fixed (non-translating). As shown in FIG. 7, the increase in epithelial scattering can be readily observed in OFDI and is spatially localized as defined by the laser beam profile. Although not illustrated in FIG. 4, the OFDI beam can be relayed to the focusing lens by a pair of galvanometers that provide two-dimensional scanning. The galvanometers may be used to generate an en face OFDI image of the sample and the epithelial burn may appear as a circle of increased scattering. The galvanometers can then be positioned and fixed so that the OFDI beam is positioned with the desired offset (as schematically shown in FIG. 4).

Exemplary Wavelength Scaling

One of the purposes of this experiment is to test the exemplary technique and method of wavelength variation and power normalization according to the present invention for achieving clinically relevant variation in the depth of laser damage. Laser wavelength may be varied from about 1375 nm to 1405 nm in 2 nm steps with laser spot size and scanning speed held constant. For each wavelength, the laser power may be adjusted so that the product $P_d \oplus \mu_a$ in Eq. 1 can be maintained as constant. This should yield lines of constant width and with damage depth ranging from approximately 0.25 to 1.5 mm.

Exemplary Scanning Velocity Scaling

One exemplary embodiment according to the present invention for affecting therapeutic depth may include scaling the scan velocity. For example, the therapy beam scan speed can be varied from 1 mm/s to 5 mm/s. Slower scan speeds allow time for heat to conduct to deeper areas of the tissue, producing deeper therapy.

Exemplary Positioning and Registration of Laser and OFDI Beams

To ensure accurate therapeutic monitoring, the spatial relationship between the OFDI sampling beam and the laser spot can be controlled.

Exemplary Endoscopic Probe Designs

Figure 11:
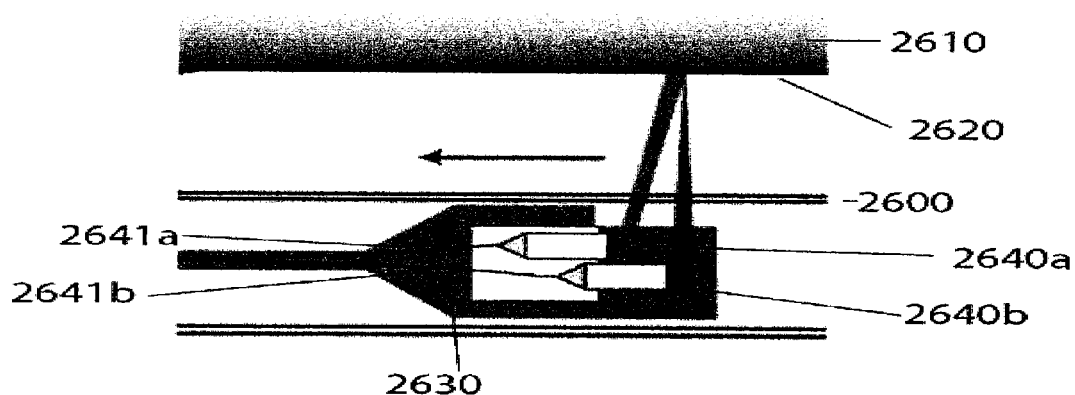
FIG. 11 is a schematic diagram of a two beam catheter probe in accordance with another exemplary embodiment of the present invention.

One exemplary embodiment of the present invention can include an endoscopic probe for comprehensive, volumetric imaging and simultaneous laser therapy, as shown in FIG. 11. For example, two beam relay optics 2640a and 2640b may be used, one of which conveys imaging light 2640b and the other therapy light 2640a. These relay optics are placed within a housing 2630 that is enclosed within a first transparent sheath 2600. A balloon centration mechanism (as described above) 2620 may be used to maintain a constant distance between the optical probe 2630 and the tissue surface 2610. Laser light and the OFDI beam may be delivered through separate optical fibers 2641a and 2641b. Each fiber may have its own relay optics to produce independently controllable spot sizes. A further exemplary embodiment of the present invention can include these relay optics designed to produce overlapping spots. The optical fibers and distal optics may be housed in a wound-wire drive shaft and placed inside a balloon-centering probe identical to the balloon sheaths.

Longitudinal scans can be activated using a computer controlled translation stage attached to the proximal end of the drive shaft. This exemplary arrangement may be the same as the arrangement which can be used for the pull-back esophageal imaging of our preliminary studies. A manual rotation of the drive shaft may be possible, as is automated rotation using an exemplary rotary coupler 2900 shown in FIG. 13. In one exemplary embodiment of the present invention, an endoscopic system may screen for disease over large fields-of-view, accurate monitoring of laser-tissue interaction, and precisely control laser therapy. One of the applications of such exemplary embodiment may be the identification and treatment of epithelial cancers and their precursors. In a further exemplary embodiment, the system can incorporate procedures and software modules than can directly link screening, monitoring, and control.

Figure 14:
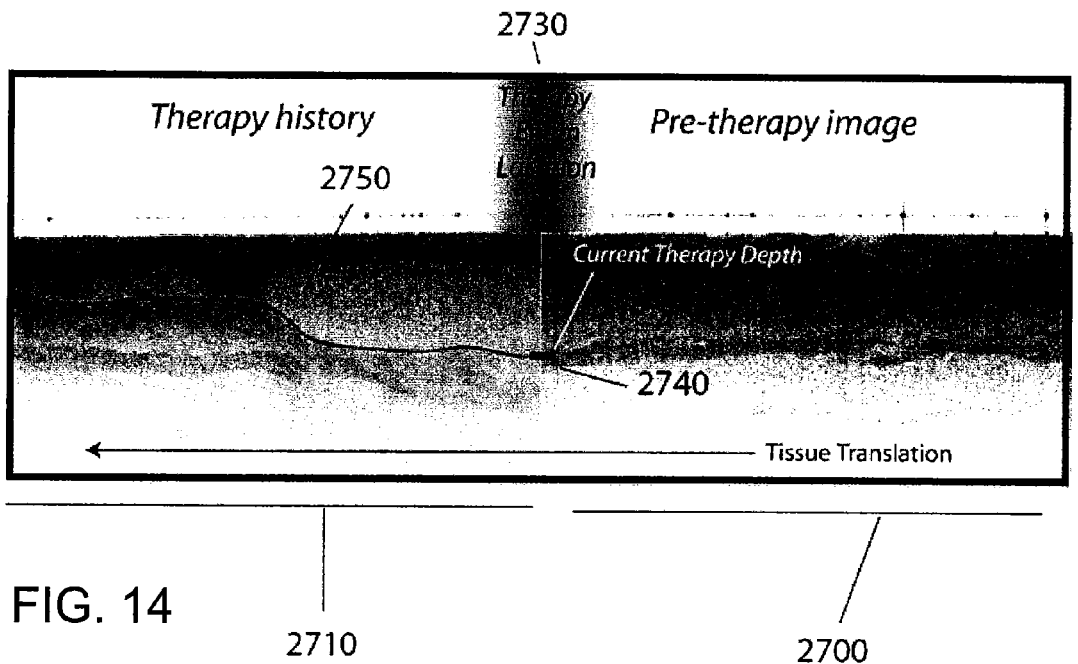
FIG. 14 is a conceptual rendering of an image which can provide feedback to a user obtained using an exemplary embodiment of the present invention.

In yet another exemplary embodiment, the system may be used to generate a high-resolution, 3-dimensional map of the entire distal esophagus to facilitate therapeutic planning. Thereafter, the use may be presented with a 'live' cross-sectional image comprising three sections, as illustrated in FIG. 14. A right section 2700 of the image may be the tissue immediately ahead of the therapeutic laser, the center 2730 of the image may be the location of the laser with a marker 2740 designating the zone of therapy, and the left section 2710 of the image may be the tissue that has already been treated. Since the three beams may be continuously scanning, the tissue may appear to move from right to left as the image updates. The user (e.g., an endoscopist) may operate a control servo to start/stop the treatment and increase or decrease the depth of therapy. By viewing the zone of treatment 2710 and looking ahead to the untreated tissue 2700, the user may be able to steer and conform the region of laser therapy to the desired target.

Figure 12:
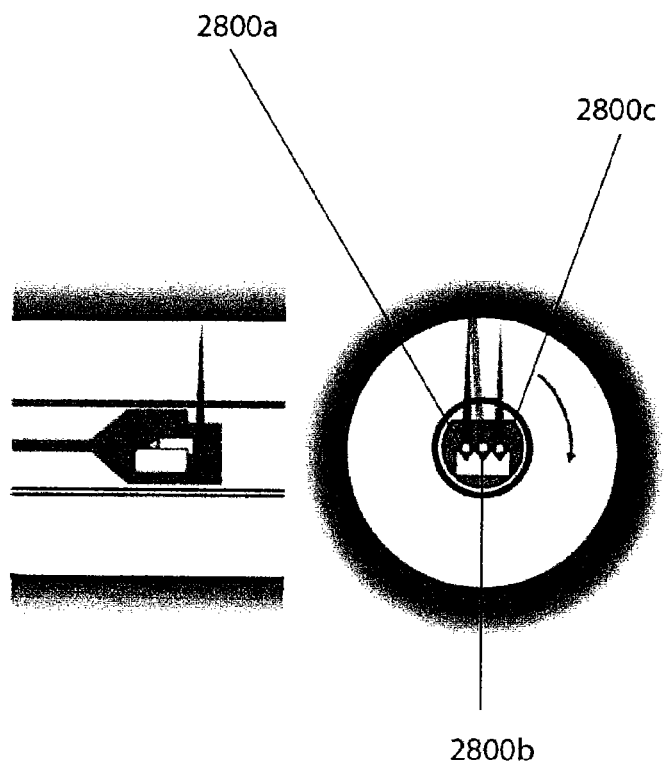
FIG. 12 is schematic side and front illustrations of a three beam catheter probe in accordance with yet another exemplary embodiment of the present invention.

An exemplary embodiment of the endoscopic probe for imaging, monitoring and laser therapy through a centering balloon according to the present invention is shown in FIG. 12. This exemplary probe can rotate to scan the esophagus circumferentially and may be longitudinally translated at a slower rate to define segments for therapy. This probe may include, e.g., three or more optical channels: a first channel 2800c for imaging the tissue prior to laser irradiation, a second channel 2800b for treatment, and a third channel 2800a for monitoring. Each optical fiber may be separately imaged transversely onto the esophageal wall through the balloon. The alignment of the resulting output beams may be such that, upon rotation in the clockwise direction, the imaging beam precedes the treatment beam sufficiently so that non-treated tissue may be sampled. The monitoring beam may be aligned to fall within the laser spot. Following initial alignment of the three beams, the optics may be bonded together with epoxy, and the alignment may be fixed.

Exemplary Rotary Junction

Figure 13:
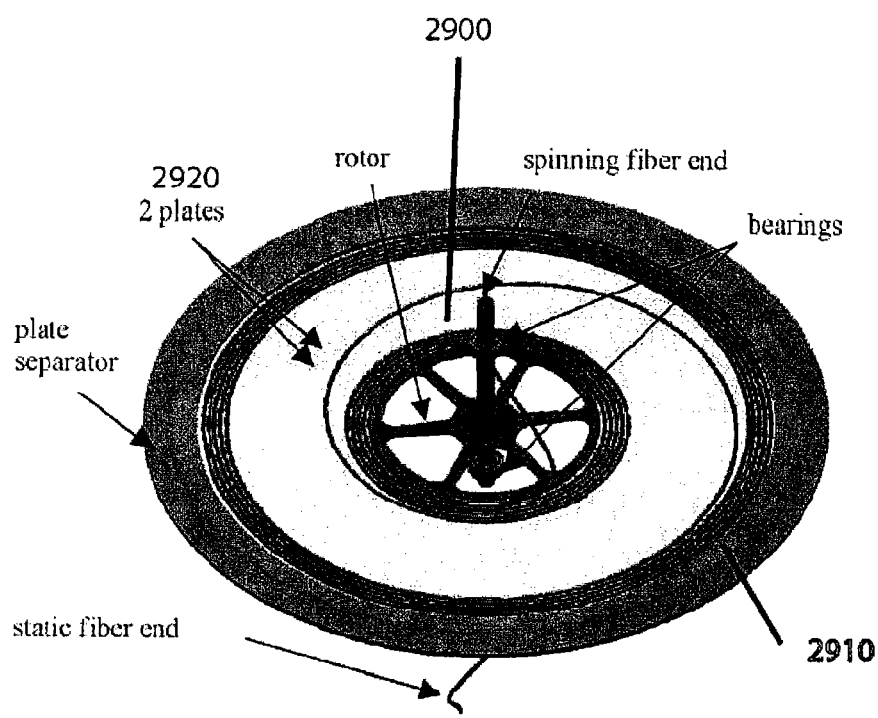
FIG. 13 is a perspective view of a watch-spring multichannel optical rotary junction in accordance with an exemplary embodiment of the present invention.

An exemplary rotational coupler according to the present invention which can connect the three-channel catheter to the OFDI system is shown in FIG. 13, and can be referred to "watch-spring" rotary junction (since it can rely on two concentric spools). For example, as the inner spool 2900 rotates in one direction, optical fiber is wound from the outer spool 2910 onto the inner spool 2900. On reversing the direction, the fiber can unwind from the inner spool. Ribbon optical fiber may be used and two parallel plates 2920 with a gap matched to the ribbon width can ensure that the windings remain flat and do not bind. The plates may be sufficiently large so that up to, e.g., 100 rotations may be possible prior to requiring counter rotation. With a 1 mm laser spot, full treatment of 6 cm long esophageal segments may be 60 revolutions. A plate diameter of less than 10 cm can be used. In addition to accommodating three optical channels, this exemplary embodiment of the arrangement and system according to the present invention can avoid the loss and back-reflections that arise from air-gap couplers.

Exemplary High-Speed Acquisition and Processing

A further exemplary embodiment of the system and arrangement according to the present invention can utilize, e.g., a high-speed imaging system. The exemplary embodiment of the digital acquisition and processing system can be based on VME-bus hardware for acquiring, processing and storing the OFDI signals in real-time. The exemplary components of such exemplary system and arrangement may comprise a VME chassis containing high-speed digitizers residing on a single-board computer and fiber-optic links to a RAID storage array. This exemplary system and arrangement can be controlled via a host processor (e.g., a personal computer). The analog OFDI signals may be digitized using wideband receivers (e.g., 12 bit, 210 MS/s) with integrated field-programmable-gate-array (FPGA) processors. Processing power, resident on the acquisition board, may be importance since the raw data rate may be 800 MB/s for the two polarization channels of the OFDI system. The FPGA processor can be configured or programmed to transform each polarization channel from the frequency-domain to a 1024-element array representing reflectivity versus depth (one A-line). This data can be passed to the single-board computer for subsequent processing and for combining the two channels prior to transferring the final data to a RAID array of hard drives. The final data storage rate may be, e.g., 400 MB/s. By striping the data across multiple hard drives, this data rate can be continuously sustained.

Software on a processing arrangement in accordance with an exemplary embodiment of the present invention can permit a user control over the exemplary system, and may enable a display of the images at a down-sampled rate in real-time. For example, the exemplary system can be used in two exemplary modes: a burst mode at full data rate, and continuous mode at half data rate. The exemplary endoscopic system and arrangement can include the components and software described above, and additional procedures (e.g., software) can be provided to program both the FPGA processor and single-board computer to facilitate the computations of phase-shift, birefringence, speckle, and Doppler signals in real-time. The combined computational capacity of the Vertex 4 Pro FPGA and quad G4 single-board computers may be ample for displaying the monitoring signal in real-time.

Exemplary Laser

Using Eq. 1, the spot size while maintaining a constant scan velocity can be doubled by using a 4-fold increase in the laser power in order to maintain a constant temperature distribution in the tissue. Doubling the scan velocity at a constant spot size should use a doubled laser power. One exemplary embodiment of a laser arrangement in accordance with the present invention can utilize a single-emitter semiconductor laser diode. Previous devices have provided more than 3 W of laser power over this spectral range using a simple external cavity design including a diffraction grating for wavelength control. The laser power and wavelength may be controlled via the host processing arrangement of the OFDI system based on an analog signal from a potentiometer. The potentiometer may be a hand-held dial that the user (e.g., an endoscopist) may use to increase or decrease the depth of laser damage.

Exemplary User Interface

The exemplary embodiment of the system and method according to the present invention can provide a user interface to the operator that includes a cross-sectional image of the tissue. The image may be continuously updated and may include views of treated and upcoming, untreated tissue as well as a designation for the zone of laser treatment as determined by the monitoring procedures. The user interface may be programmed on the host processing arrangement, and can use computational results from the FPGA processor and single-board computer. Images and laser parameters may be archived to the RAID array.

Figure 15:
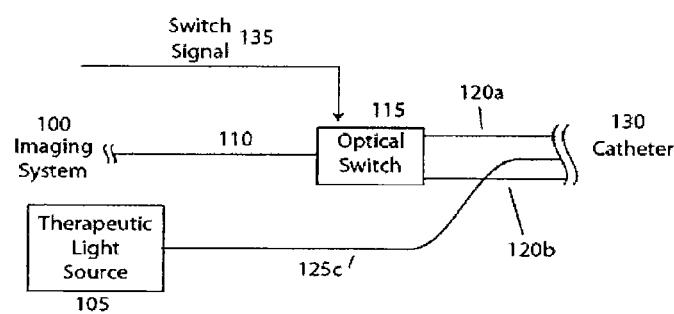
FIG. 15 is a block diagram of a sample arm of an OFDI system incorporating an optical switch in accordance with a further exemplary embodiment of the present invention.

In one further exemplary embodiment of the present invention, the imaging system/arrangement 100 can be connected to a three-fiber probe using an optical switch 115 as shown in a block diagram of FIG. 15. The exemplary probe, such as that described above with reference to FIG. 12, can include two imaging fibers and one therapy fiber. The switch 115 can alternately couple imaging light to one of the two imaging fibers 120*a*, 120*b* which can be used to acquire re-therapy images and, e.g., during-therapy imaging. A therapeutic light source 105 may connect directly to the therapy fiber 125*c*. The fibers can be connected to the catheter 130, which can be, e.g., the exemplary catheter shown FIG. 12. A signal from the imaging system 100 can control the state of the optical switch 115.

Figure 16:
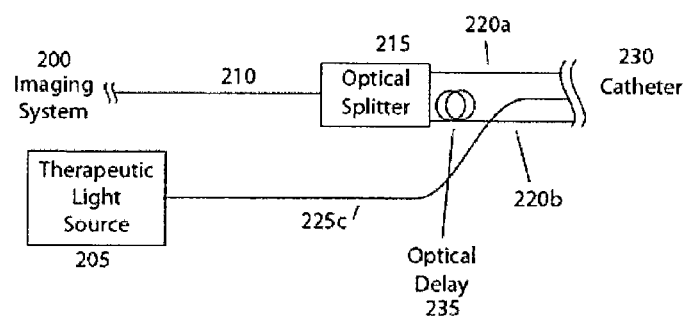
FIG. 16 is a block diagram of the sample arm of the OFDI system incorporating an optical splitter in accordance with a still further exemplary embodiment of the present invention.

In yet another exemplary embodiment according to the present invention shown in FIG. 16, the exemplary imaging system/arrangement 200 can be coupled to an exemplary three-port catheter such as one shown in FIG. 12 via an optical splitter 215 that can couple light to both of two imaging fibers 220*a*, 220*b*. This exemplary imaging system can separate the image signal from each using path-length encoding techniques. To generate the differential path length, an optical delay 235 may be placed in one fiber 220*b* or multiple fibers. The therapeutic light source 205 can be coupled directly or indirectly to the therapy fier 225*c* of the catheter.

Figure 17:
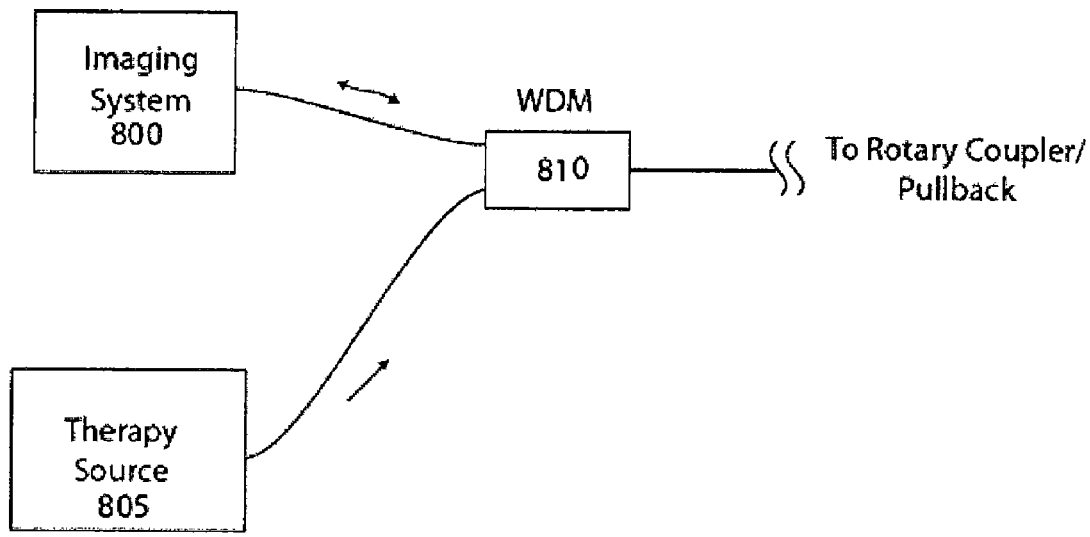
FIG. 17 is a block diagram of the sample arm of the OFDI system incorporating a single wavelength-division multiplexer in accordance with yet further exemplary embodiment of the present invention.

In still another exemplary embodiment of the exemplary imaging system/arrangement 800 according to the present invention shown in FIG. 17, light may be combined with the therapy source 805 using a single wavelength-division multiplexer 810. The combined light may be coupled to a single fiber rotary coupler, and then to an exemplary single fiber catheter such as the catheter shown in FIG. 21.

Figure 18:
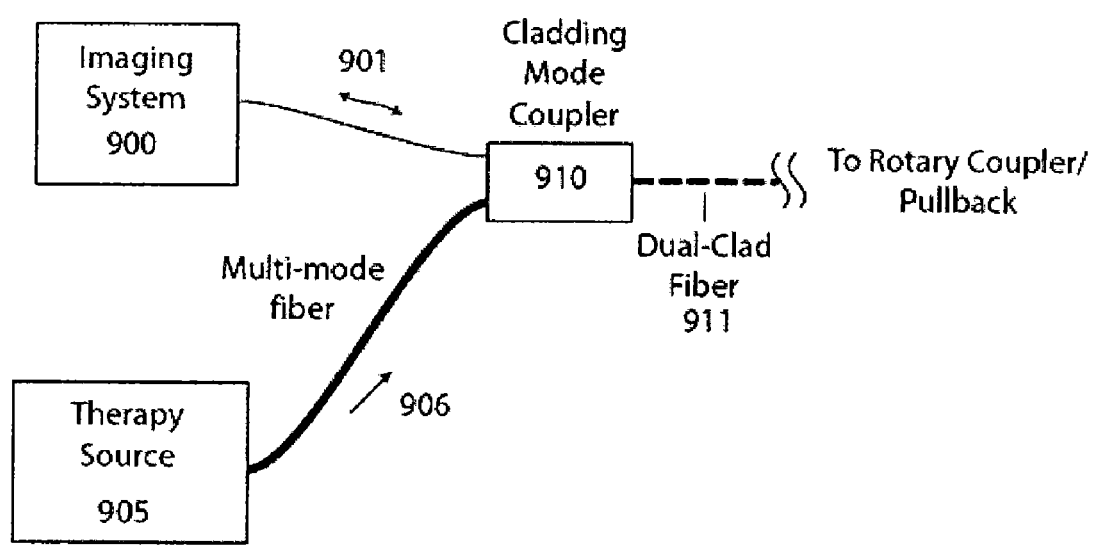
FIG. 18 is a block diagram of the sample arm of the OFDI system incorporating a cladding mode coupler and a dual-clad fiber in accordance with still another exemplary embodiment of the present invention.

In a further exemplary embodiment of the imaging system/arrangement 900 according to the present invention shown in FIG. 18, light may be combined with the therapy light 905 using a cladding mode coupler that couples the imaging system 900 light from the single mode fiber 901 to the single mode core of a dual-clad fiber 911 and the therapy light from a multimode fiber 906 to the cladding mode of a dual-clad fiber 911.

Figure 19:
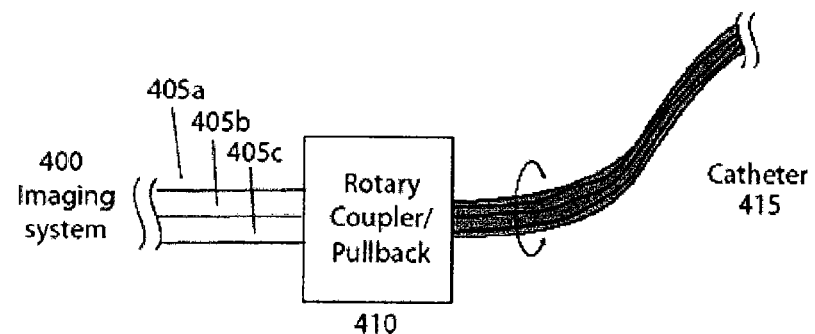
FIG. 19 is a block diagram of a three-port rotary coupler and catheter in accordance with an exemplary embodiment of the present invention.

FIG. 19 shows exemplary connections between a system 400 with three output fibers 405*a*, 405*b*, 405*c*, such as one shown schematically in, e.g., FIGS. 15 and 16, and a three-port catheter 415, such as one shown in FIG. 12 via a multi-channel rotary coupler 410, such as one shown in FIG. 13.

Figure 20:
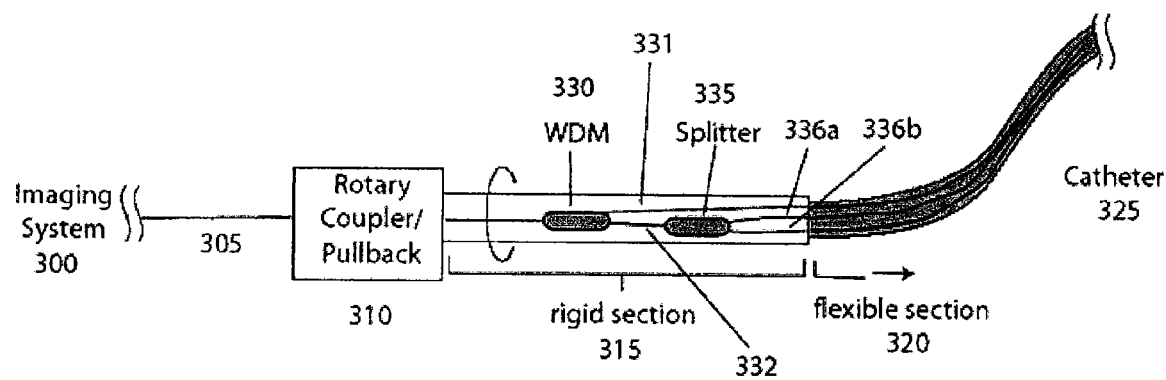
FIG. 20 is a block diagram of a single-fiber rotary coupler with subsequent demultiplexing of the therapy light and capable of splitting of imaging light in accordance with another exemplary embodiment of the present invention.

FIG. 20 shows a schematic diagram of an exemplary system 300 according to the present invention in which a single fiber 305 containing both the imaging light and therapy light may be coupled to a single-channel rotary coupler 310. For example, after the rotary coupler 310, the light can be divided by a wavelength-division multiplexer (WDM) 330 that separates the imaging light onto a first fiber 332 and the therapy light onto a second fiber 331. The imaging light may further be separated using an optical splitter 335 that greats two imaging ports 336*a* and 336*b*. The fibers 31, 336*a*, 336*b* can be connected to a three-port catheter 325 design such as that shown in FIG. 12. The catheter section 320 may be flexible allowing endoscopic insertion and the section containing a WDM 330 and a splitter 335 can be enclosed within a rigid tube 315 to protect these components.

Figure 21:
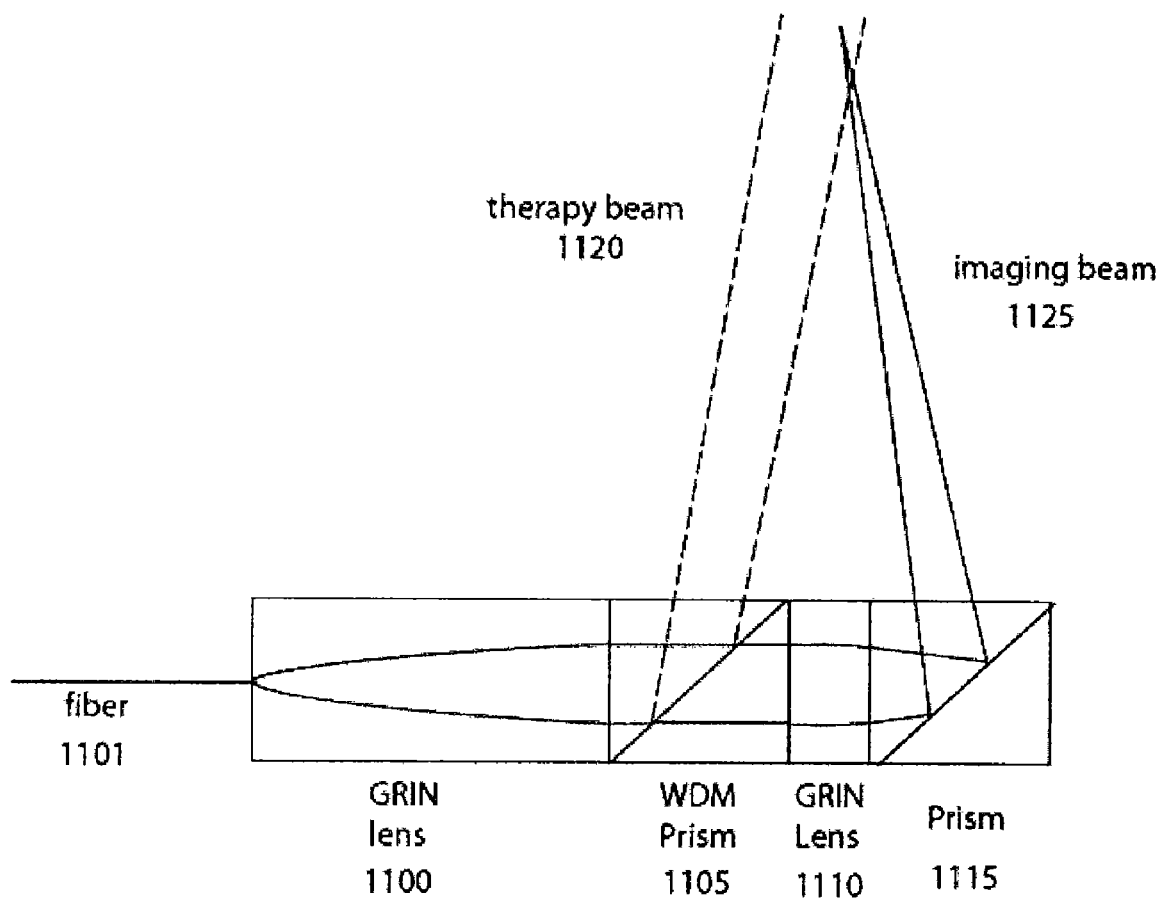
FIG. 21 is a schematic diagram and usage of a two-beam in-line catheter probe in accordance with an exemplary embodiment of the present invention.

FIG. 21 shows a side view of an exemplary embodiment of a distal optics arrangement according to the present invention that may create a single imaging beam 1125 and a separate therapy beam 1120 from a single-mode fiber 1101. For example, the light from the fiber containing both imaging and therapy light can first be focused by a first GRIN lens 1100. The light is then passed into a wavelength-division multiplexing prism 1105 that can direct the therapy light wavelengths upward to create the therapy beam 1120, and transmits the imaging light wavelengths to a second GRIN lens 1110, which can alternately focus the imaging light and directs it to a final prism 1115 that directs the imaging beam 1125 upward. The angle of the prisms 1105 and 1115 may be such that the beams are made to overlap at the appropriate distance from the device.

Figure 22:
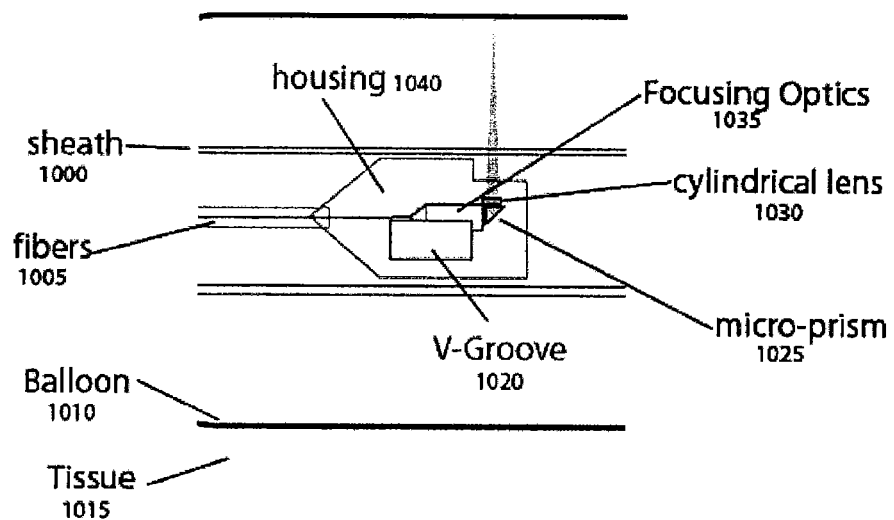
FIG. 22 are front and side illustrations of a three-beam catheter probe and balloon catheter in accordance with an exemplary embodiment of the present invention.
Figure 22:
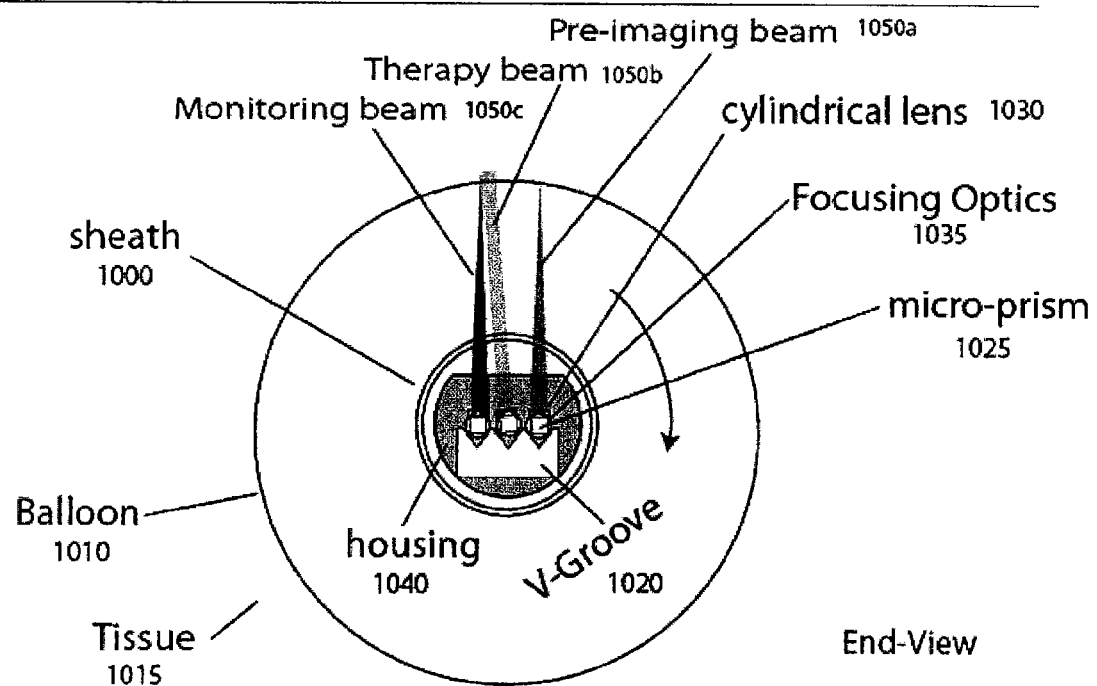

FIG. 22 shows side and front views of an exemplary embodiment of a three-port catheter in accordance with the present invention. The exemplary catheter can include three fibers 1005 that connect to three sets of focusing optics 1035 contained in a V-groove 1020 inside a housing 1040. The focusing optics can provide beam focusing. Micro-prisms 1025 can redirect the optical beam upward through a cylindrical lens 1030 that corrects for astigmatism induced by the transparent sheath 1000. A balloon 1010 centration mechanism may be used to maintain centering of the optics 1035 within the luminal tissue 1015. In the end-view, the monitoring beam 1050*c*, therapy beam 1050*b*, and pre-imaging beam 1050*a* can be seen. The housing 1040 can be adapted to rotate by a multichannel rotary coupler such as one shown in FIG. 13.

Figure 23:
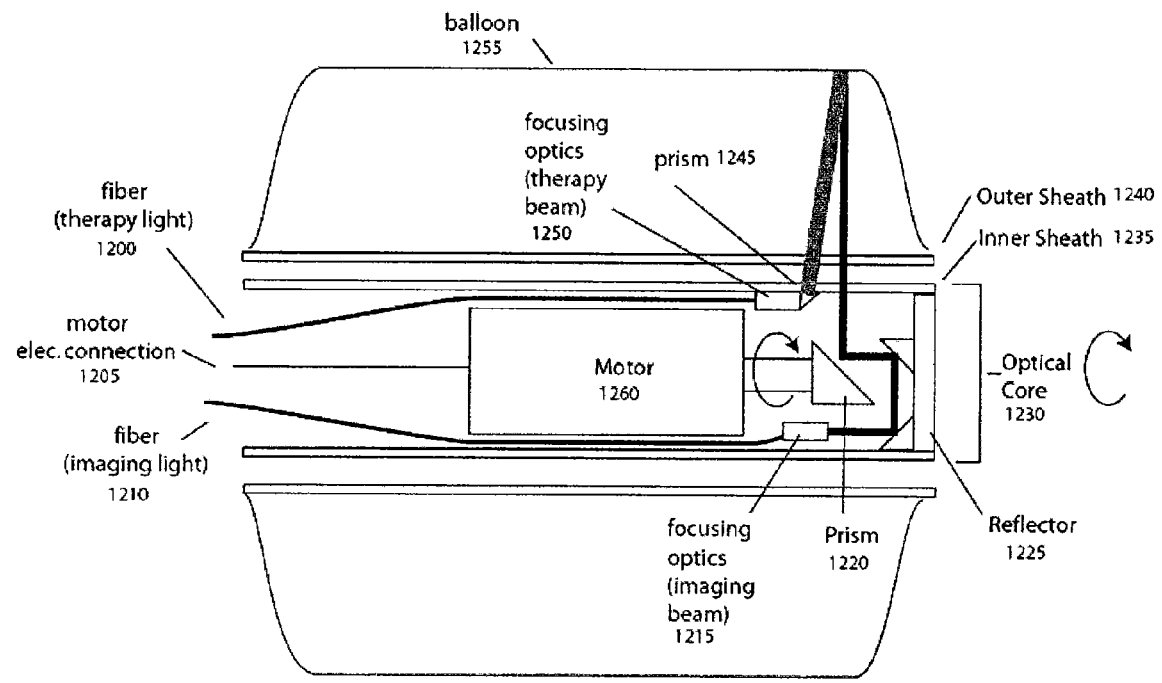
FIG. 23 is a side view of a micro-motor-based arrangement capable of generating a slowly rotatable therapy beam and fast scanning imaging beam in accordance with an exemplary embodiment of the present invention.

FIG. 23 shows a side view of an exemplary embodiment of a catheter in accordance with the present invention which can utilize a miniature motor 1260 to achieve rotation of the imaging beam. For example, the motor 1260 can be enclosed within a transparent sheath 1235. The rotation of the motor shaft can rotate a prism 1220. The imaging light can be coupled to the distal optics via a fiber 1210, where the light can be focused by focusing optics 1215, and reflected onto the prism 1220 by a reflector 1225. The rotation of the prism 1220 sweeps the imaging beam circumferentially. The motor electrical connections 1205 can be achieved through the same lumen as the fiber 1210. The therapy light is coupled to the distal optics on fiber 1200. This therapy light may be focused using focusing optics 1250, and directed sideways by prism 1245 at a fixed rotational angle relative to the inner sheath 1235. The imaging beam thus sweeps through the fixed therapy spot. The translation of the therapy spot is achieved by rotation of the entire inner sheath 1235 within the outer sheath 1240. This exemplary rotation can be achieved through the use of a multi-channel rotary coupler such as a coupler shown in FIG. 13. The catheter can use a balloon 1255 for centration of an optical core 1230.

Figure 24:
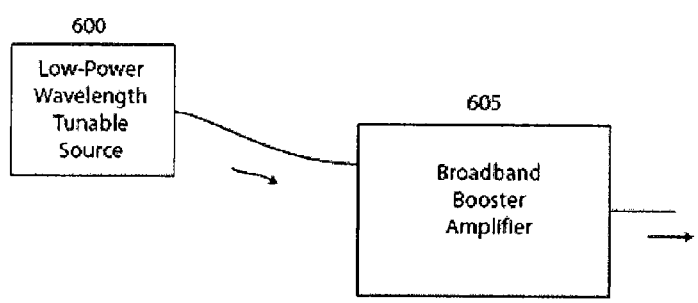
FIG. 24 is a block diagram of a therapy source incorporating a low power tunable source followed by a broadband booster amplifier in accordance with an exemplary embodiment of the present invention.

FIG. 24 shows a block diagram of an exemplary embodiment of a laser therapy source according to the present invention with wavelength tunability utilizing a low power wavelength tunable source 600, followed by a broadband booster amplifier 605 to increase the optical power.

Figure 25:
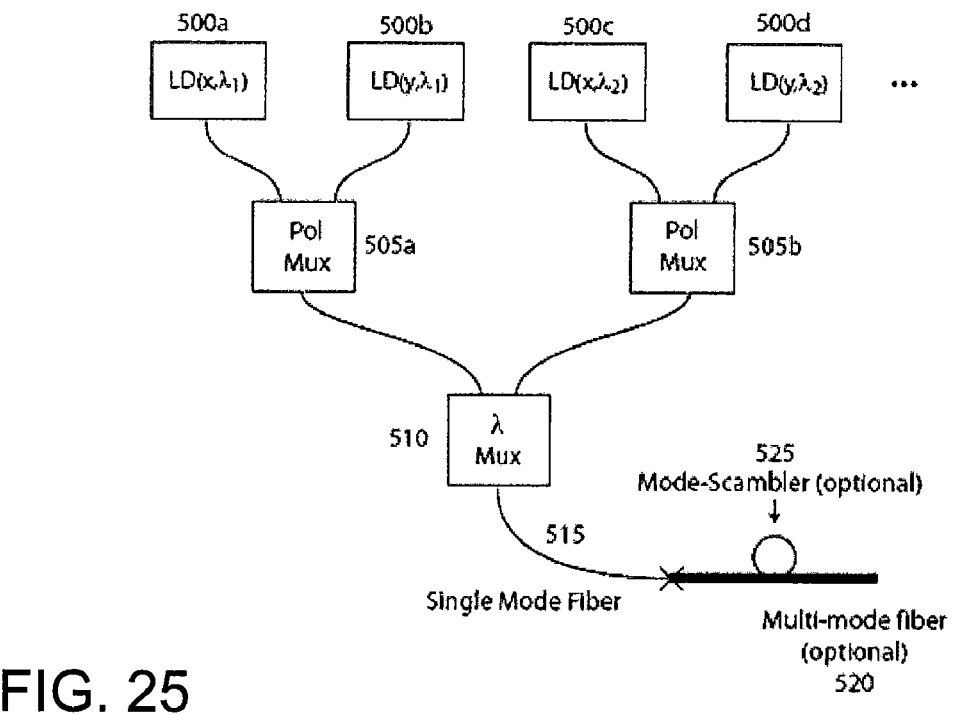
FIG. 25 is a block diagram of a therapy source incorporating multiple laser diodes (LDs) at difference wavelengths and polarizations in accordance with another exemplary embodiment of the present invention.

FIG. 25 shows a block and functional diagram of an exemplary embodiment of a laser therapy source incorporating multiple laser diodes 500*a*, 500*b*, 500*c*, 500*d* at difference wavelengths and polarizations, and the exemplary procedure to implement such arrangement. For example, the light can be combined by the polarization multiplexers 505*a*, 505*b* and wavelength division multiplexers 510 to a single mode fiber 515. Optionally, the light can be coupled to a multimode fiber 520. A fast mode scrambler 525 can be used to scramble the transverse mode pattern output from the multi-mode fiber at a fast rate. Other source arrangements which can output light on a single mode fiber can use a similar design to couple light to a multimode fiber.

Figure 26:
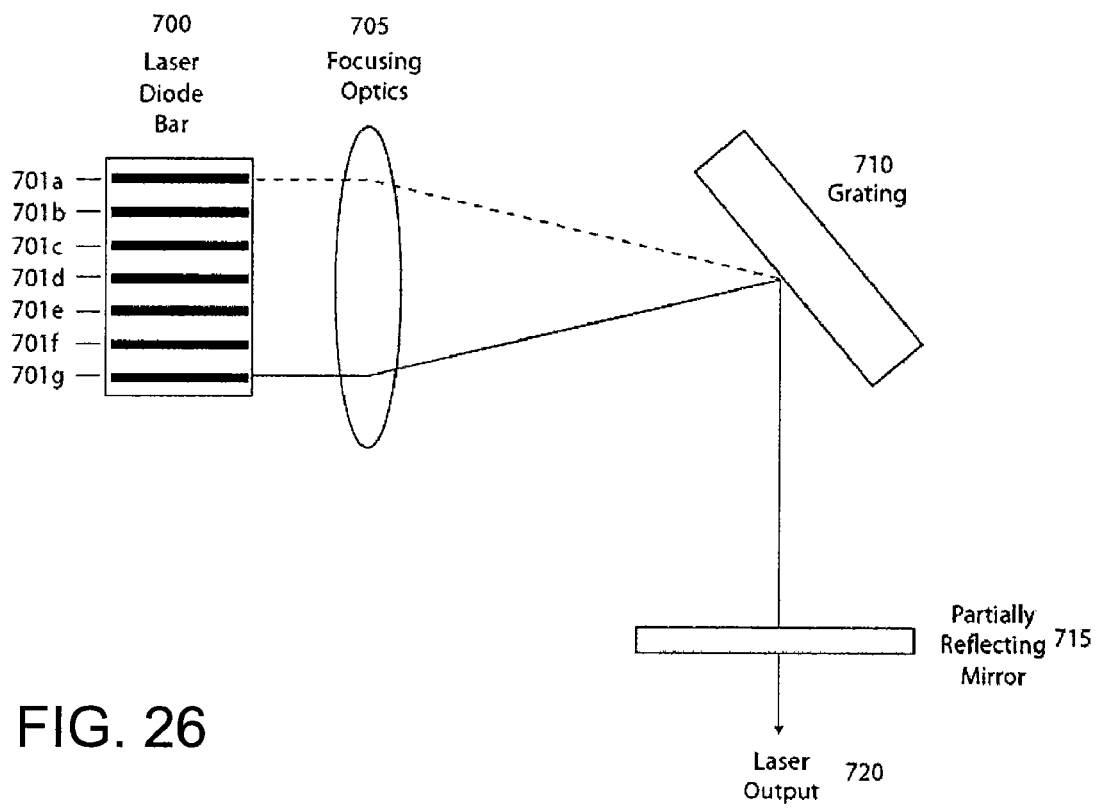
FIG. 26 is an illustration of a wavelength-tunable therapy source incorporating a laser diode bar and results generated thereby in accordance with an exemplary embodiment of the present invention.

FIG. 26 shows an exemplary embodiment of a therapy light source and use thereof according to the present invention. For example, a laser diode bar 700 can be used with multiple wavelengths 701a-g. Each waveguide can be coupled to a free-space laser cavity through a lens apparatus 705 and a grating 710 and a partially reflecting end mirror 715. Because of the wavelength dispersion of the grating, the laser formed by each waveguide lases at a different wavelength. Thus, by adjusting the drive current to each of the waveguides 701a-g, the laser output 720 power and spectral shape can be adjusted.

Figure 28:
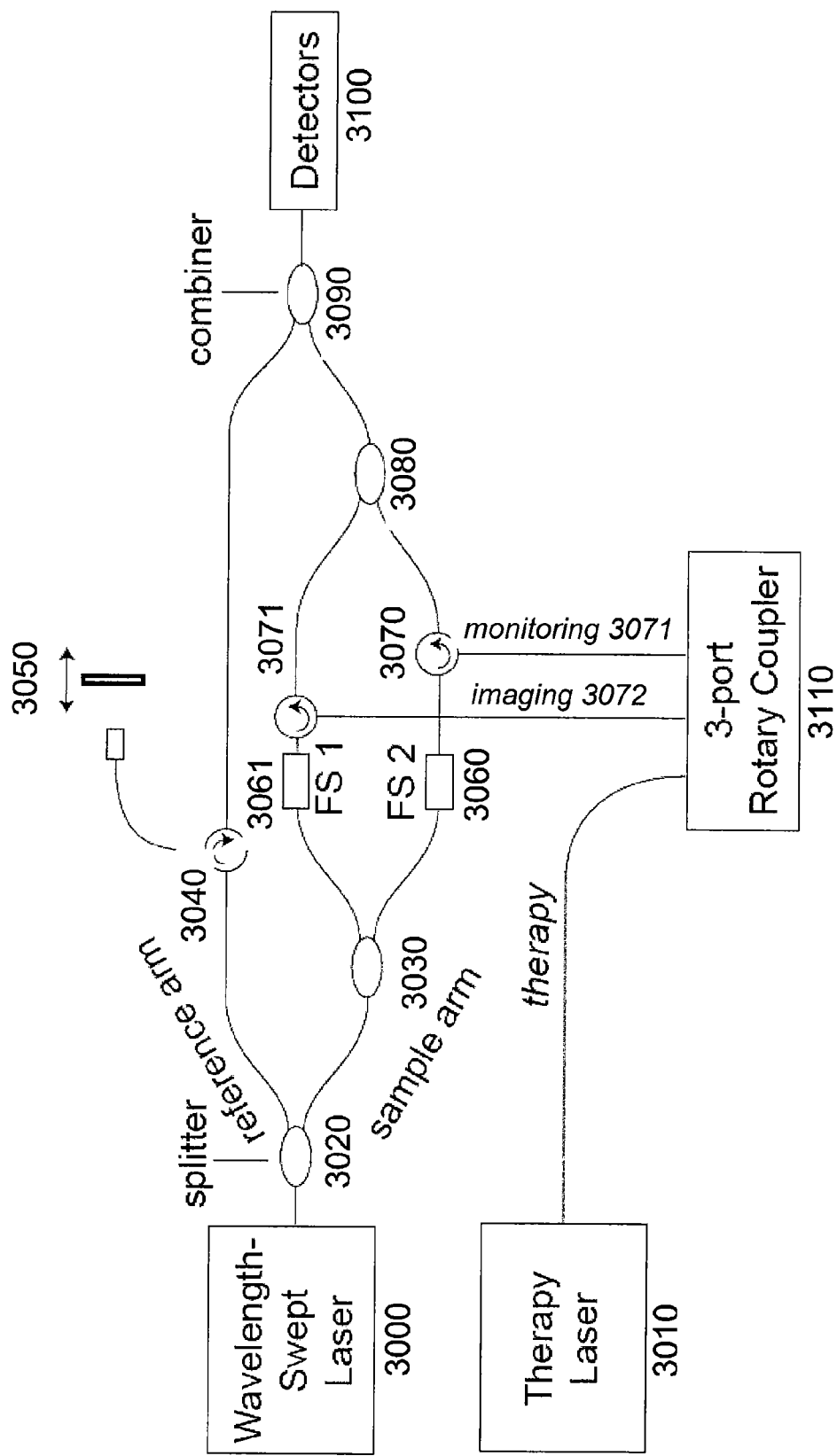
FIG. 28 is a schematic diagram of a further exemplary embodiment of the OFDI system according to the present invention which can be used to detect both the imaging and monitoring signals via acousto-optic frequency shifters.

In a further exemplary embodiment according to the present invention, a single OFDI system can be modified to facilitate a detection of both the imaging and monitoring signals through the use of acousto-optic frequency shifters as shown in FIG. 28. For example, a wavelength swept laser source 3000 can be separated by a first splitter 3020 to produce a sample arm path and reference arm path. The sample arm path is further separated by a second splitter 3030, with a first output of this splitter being directed to a first frequency shifter 3061 and a second output being directed to a second frequency shifter 3060. Each of the frequency shifters can be driven with a separate frequency. The light from the first frequency shifter 3061 can be coupled through an optical circulator 3071 to the imaging fiber 3072 of a three-fiber rotary coupler 3110 like that shown in FIG. 13. The light from the second frequency shifter 3060 may be coupled through a circulator 3070 to a monitoring fiber 3073 of the same rotary coupler.

A separate therapy laser 3010 can be coupled to the third therapy fiber. The returned light on the imaging fiber 3072 and monitoring fiber 3073 may be recombined at an optical combiner 2080, and mixed with the reference arm light at a second combiner 3090 with the output directed to a set of detectors 3100. Due to the frequency shifters, the interference signal due to the imaging light and the interference signal due to the monitoring light are encoded at separate carrier frequencies and can be separated through conventional frequency domain techniques.

Figure 29A:
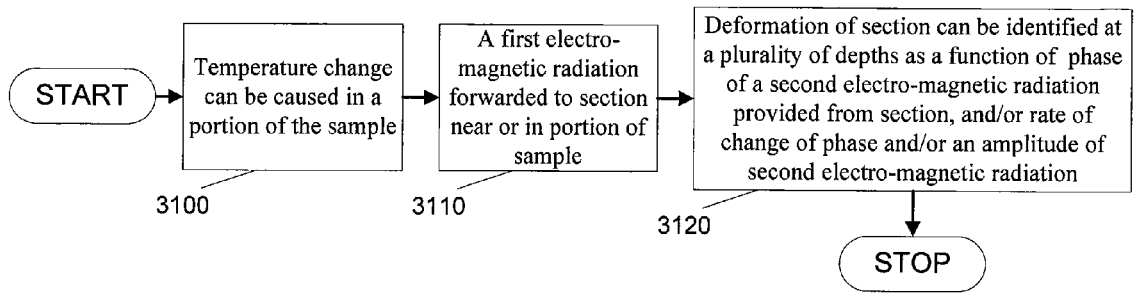
FIG. 29A is a flow diagram of an exemplary embodiment of a method for obtaining information associated with at least one portion of a sample according to the present invention.

FIG. 29A shows a flow diagram of an exemplary embodiment of a method for obtaining information associated with at least one portion of a sample according to the present invention. For example, a temperature change can be caused in the portion of the sample in step 3100. At least one first electromagnetic radiation can be forwarded to a section near or in the portion of the sample in step 3110. A deformation of the section can be identified at a plurality of depths as a function of (i) a phase of at least one second electro-magnetic radiation provided from the section, and/or (ii) a rate of change of the phase and/or an amplitude of the second electro-magnetic radiation in step 3120.

Figure 29B:
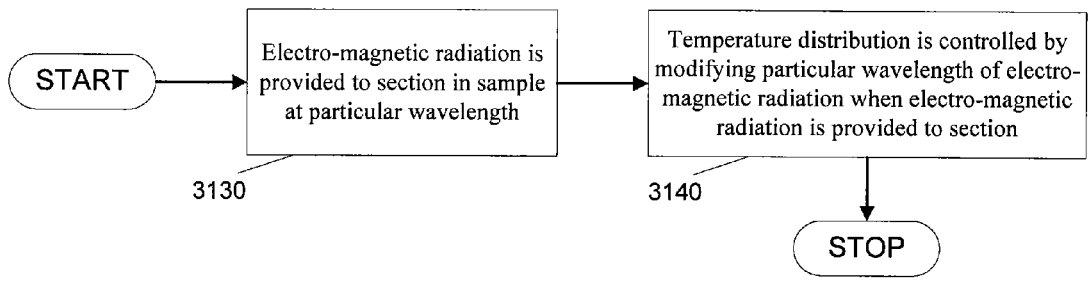
FIG. 29B is a flow diagram of another exemplary embodiment of the method for controlling a temperature distribution in the sample according to the present invention.

FIG. 29B shows a flow diagram of another exemplary embodiment of the method for controlling a temperature distribution in the sample according to the present invention. For example, an electro-magnetic radiation can be provided to the section in the sample at a particular wavelength in step 3130. The temperature distribution can be controlled by modifying the particular wavelength of the electro-magnetic radiation when the electro-magnetic radiation can be provided to the section in step 3140.

Figure 29C:
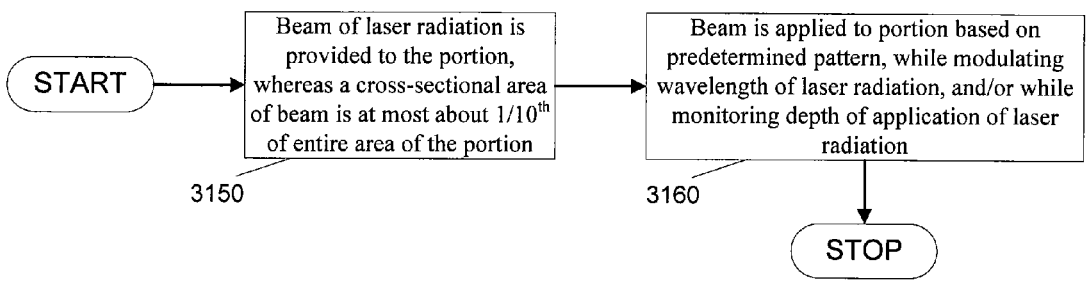
FIG. 29C is a flow diagram of yet another exemplary embodiment of the method for applying a laser radiation to at least one portion of a biological structure according to the present invention.

FIG. 29C illustrates a flow diagram of yet another exemplary embodiment of the method for applying a laser radiation to at least one portion of a biological structure according to the present invention. For example, a beam of the laser radiation can be provided to the portion in step 3150, whereas a cross-sectional area of the beam is at most about $1/10^{th}$ of an entire area of the at least one portion. In step 3160, the beam can be applied to the portion (I) based on a predetermined pattern, (II) while modulating a wavelength of the laser radiation, and/or (III) while monitoring a depth of the application of the laser radiation.

EXEMPLARY REFERENCES

1. Devesa S S, Blot W J and Fraumeni J F, Jr. Changing patterns in the incidence of esophageal and gastric carcinoma in the United States. Cancer 1998; 83:2049-2053.
2. Barr H, Stone N and Rembacken B. Endoscopic therapy for Barrett's esophagus. Gut 2005; 54:875-884.
3. Johnston M H. Technology insight: ablative techniques for Barrett's esophagus—current and emerging trends. Nature Clinical Practice Gastroenterology & Hepatology 2005; 2:323-330.
4. Falk G W, Chittajallu R, Goldblum J R, Biscotti C V, Geisinger K R, Petras R E, Birgisson S, Rice T W and Richter J E. Surveillance of patients with Barrett's esophagus for dysplasia and cancer with balloon cytology. Gastroenterology 1997; 112:1787-1797.
5. Spechler S J. Barrett's esophagus: should we brush off this ballooning problem? Gastroenterology 1997; 112:2138-2142.
6. Kubba A K, Poole N A and Watson A. Role of p53 assessment in management of Barrett's esophagus. Dig Dis Sci 1999; 44:659-667.
7. Reid B J. p53 and neoplastic progression in Barrett's esophagus. Am J Gastroenterol 2001; 96:1321-1323.
8. Sharma P, Weston A P, Topalovski M, Cheman R, Bhattacharyya A, Sampliner R E. Magnification chromoendoscopy for the detection of intestinal metaplasia and dysplasia in Barrett's oesophagus, GUT 2003; 52: 24-27.
9. Kuipers E J and Haringsma J. Diagnostic and therapeutic endoscopy. Journal of Surgical Oncology 2005; 92:203-209.
10. Georgakoudi I, Jacobson B C, Van Dam J, Backman V, Wallace M B, Muller M G, Zhang Q, Badizadegan K, Sun D, Thomas G A, Perelman L T and Feld M S. Fluorescence, reflectance, and light-scattering spectroscopy for evaluating dysplasia in patients with Barrett's esophagus. Gastroenterology 2001; 120:1620-1629.
11. Adrain A L, Ter H C, Cassidy M J, Schiano T D, Liu J B and Miller L S. High-resolution endoluminal zoography is a sensitive modality for the identification of Barrett's metaplasia. Gastrointest Endosc 1997; 46:147-151.
12. Canto M I. Vital staining and Barrett's esophagus. Gastrointest Endosc 1999; 49:S12-16.
13. Huang D, Swanson E A, Lin C P, Schuman J S, Stinson W G, Chang W, Hee M R, Flotte T, Gregory K, Puliafito C A and Fujimoto J G. Optical coherence tomography. Science 1991; 254:1178-1181.
14. Tearney G J, Brezinski M E, Bouma B E, Boppart S A, Pitvis C, Southern J F and Fujimoto J G. In vivo endoscopic optical biopsy with optical coherence tomography. Science 1997; 276:2037-2039.
15. Evans J A, Poneros J M, Bouma B E, Bressner J, Halpern E F, Shishkov M, Lauwers G Y, Mino-Kenudson M, Nishioka N S and Tearney G J. Optical Coherence Tomography to Identify Intramucosal Carcinoma and High Grade Dysplasia in Barrett's Esophagus. Clinical Gastroenterology and Hepatology 2005; 4:38-43.

16. Poneros J M, Brand S, Bouma B E, Tearney G J, Compton C C and Nishioka N S. Diagnosis of Specialized Intestinal Metaplasia by Optical Coherence Tomography. Gastroenterology 2001; 120:7-12.
17. Brand S, Poneros J M, Bouma B E, Tearney G J, Compton C C and Nishioka N S. Optical Coherent Tomography in the Gastrointestinal Tract. Endoscopy 2000; 32:796-803.
18. de Boer J F, Cense B, Park B H, Pierce M C, Tearney G J and Bouma B E. Improved signal-to-noise ratio in spectral-domain compared with time-domain optical coherence tomography. Optics Letters 2003; 28:2067-2069.
19. Choma M A, Sarunic M V, Changhuei Y and Izatt J A. Sensitivity advantage of swept source and Fourier domain optical coherence tomography. Optics Express 2003; 11:2183-2189.
20. Leitgeb R, Hitzenberger C K and Fercher A F. Performance of Fourier domain vs. time domain optical coherence tomography. Optics Express 2003; 11:889-894.
21. Yun S H, Tearney G J, de Boer J F, Iftimia N and Bouma B E. High-speed optical frequency-domain imaging. Optics Express 2003; 11:2953-2963.
22. Yun S H, Boudoux C, Tearney G J and Bouma B E. High-speed wavelength-swept semiconductor laser with a polygon-scanner-based wavelength filter. Optics Letters 2003; 28:1981-1983.
23. Oh W Y, Yun S H, Tearney G J and Bouma B E. 115 kHz tuning repetition rate ultrahigh-speed wavelength-swept semiconductor laser. Optics Letters 2005; 30:3159-3161.
24. Vakoc B J, Yun S H, de Boer J F, Tearney G J and Bouma B E. Phase-resolved optical frequency domain imaging. Optics Express 2005; 13:5483-5493.
25. Brown S B, Brown E A and Walker I. The present and future role of photodynamic therapy in cancer treatment. Lancet Oncol 2004; 5:497-508.
26. van den Boogert J, van Hillegersberg R, Siersema P D, de Bruin R W and Tilanus H W. Endoscopic ablation therapy for Barrett's esophagus with high-grade dysplasia: a review. Am J Gastroenterol 1999; 94:1153-1160.
27. Sampliner R E, Fennerty B and Garewal H S. Reversal of Barrett's esophagus with acid suppression and multipolar electrocoagulation: preliminary results. Gastrointest Endosc 1996; 44:532-535.
28. Sampliner R E. Endoscopic ablative therapy for Barrett's esophagus: current status. Gastrointest Endosc 2004; 59:66-69.
29. Soetikno R M, Gotoda T, Nakanishi Y and Soehendra N. Endoscopic mucosal resection. Gastrointest Endosc 2003; 57:567-579.
30. Ganz R A, Utley D S, Stern R A, Jackson J, Batts K P and Termin P. Complete ablation of esophageal epithelium with a balloon-based bipolar electrode: a phased evaluation in the porcine and in the human esophagus. Gastrointest Endosc 2004; 60:1002-1010.
31. Mark H. Johnston, Brooks D. Cash, Cathy A. Dykes, Halisha S. Mays and Lavonne R. Johnston Cryoablation of Dysplasia in Barrett's Esophagus (BE) and Early Stage Esophageal Cancer. Gastrointest Endosc 2006; 63: AB223.
32. Overholt B F, Panjehpour M and Haydek J M. Photodynamic therapy for Barrett's esophagus: follow-up in 100 patients. Gastrointest Endosc 1999; 49:1-7.
33. Vogel A and Venugopalan V. Mechanisms of pulsed laser ablation of biological tissues. Chemical Reviews 2003; 103:2079-2079.
34. McKenzie A L. Physics of thermal processes in laser-tissue interactions. Physics in Medicine & Biology 1990; 35:1175-1209.
35. Anderson R R and Parrish J A. Selective photothermolysis: precise microsurgery by selective absorption of pulsed radiation. Science 1983; 220:524-527.
36. Jacques S L. Role of tissue optics and pulse duration on tissue effects during high-power laser irradiation. Applied Optics 1993; 32:2447-2454.
37. Nahen K and Vogel A. Investigations on acoustic on-line monitoring of IR laser ablation of burned skin. Lasers in Surgery & Medicine 1999; 25:69-78.
38. Jerath M R, Kaisig D, Rylander H G, 3rd and Welch A J. Calibrated real-time control of lesion size based on reflectance images. Applied Optics 1993; 32:1200-1209.
39. Jerath M R, Gardner C M, Rylander H G, 3rd and Welch A J. Dynamic optical property changes: implications for reflectance feedback control of photocoagulation. Journal of Photochemistry & Photobiology B—Biology 1992; 16:113-126.
40. Deckelbaum L I. Coronary laser angioplasty. Lasers in Surgery & Medicine 1994; 14:101-110.
41. Kim B M, Feit M D, Rubenchik A M, Mammini B M and Da Silva L B. Optical feedback signal for ultra short laser pulse ablation of tissue. Applied Surface Science 1998; 127-129:857-862.
42. Brinkmann R, Hansen C, Mohrenstecher D, Scheu M and Birngruber R. Analysis of cavitation dynamics during pulsed laser tissue ablation by optical on-line monitoring. Selected Topics in Quantum Electronics, IEEE Journal of 1996; 2:826.
43. Whelan W M, Davidson S R H, Chin L C L and Vitkin I A. A Novel Strategy For Monitoring Laser Thermal Therapy Based on Changes in Optothermal Properties of Heated Tissues. International Journal of Thermophysics 2005; 26:233-241.
44. Boppart S A, Herrmann J, Pitris C, Stamper D L, Brezinski M E and Fujimoto J G. High-resolution optical coherence tomography-guided laser ablation of surgical tissue. Journal of Surgical Research 1999; 82:275-284.
45. Thomsen S L, Jacques S L and Flock S T. Microscopic correlates of macroscopic optical property changes during thermal coagulation of myocardium. Proceedings of the SPIE 1990; 1202:2-11.
46. Maitland D J and Walsh J T, Jr. Quantitative measurements of linear birefringence during heating of native collagen. Lasers Surg Med 1997; 20:310-318.
47. Kimel S, Svaasand L O, Hammer-Wilson M, Schell M J, Milner T E, Nelson J S and Berns M W. Differential vascular response to laser photothermolysis. Journal of Investigative Dermatology 1994; 103:693-700.
48. Khan M H, Sink R K, Manstein D, Eimerl D and Anderson R R. Intradermally focused infrared laser pulses: Thermal effects at defined tissue depths. Lasers in Surgery and Medicine 2005; 36:270-280.
49. Neumann R A, Knobler R M, Pieczkowski F and Gebhart W. Enzyme histochemical analysis of cell viability after argon laser-induced coagulation necrosis of the skin. Journal of the American Academy of Dermatology 1991; 25:991-998.
50. Nadkarni S, Helg T, Bouma B E, Chan R C, Minsky M S, Chau A H, Motz J, Houser S L and Tearney G J. Characterization of atherosclerotic plaques by laser speckle analysis. Circulation 2005; 112:885-892.
51. Zimnyakov D A, Agafonov D N, Sviridov A P, Omel'chenko A I, Kuznetsova L V and Bagratashvili V N. Speckle-contrast monitoring of tissue thermal modification. Appl Opt 2002; 41:5989-5996.
52. Pierce M C, Sheridan R L, Park B H, Cense B and de Boer J F. Collagen denaturation can be quantified in burned human skin using polarization-sensitive optical coherence tomography. Burns 2004; 30:511-517.
53. de Boer J F, Milner T E, van Gemert M J C and Nelson J S. Two-dimensional birefringence imaging in biological tissue using polarization sensitive optical coherence tomography. Optics Letters 1997; 22:934-936.
54. Morelli J G, Tan O T, Garden J, Margolis R, Seki Y, Boll J, Carney J M, Anderson R R, Furumoto H and Parrish J A. Tunable dye laser (577 nm) treatment of port wine stains. Lasers Surg Med 1986; 6:94-99.
55. Chen Z P, Milner T E, Dave D and Nelson J S. Optical Doppler tomographic imaging of fluid flow velocity in highly scattering media. Optics Letters 1997; 22:64-66.
56. Izatt J A, Kulkami M D, Yazdanfar S, Barton J K and Welch A J. In vivo bidirectional color Doppler flow imaging of picoliter blood volumes using optical coherence tomography. Optics Letters 1997; 22:1439.
57. Barton J K, Welch A J and Izatt J A. Investigating pulsed dye laser-blood vessel interaction with color Doppler optical coherence tomography. Optics Express 1998; 3:251-256.
58. French P M W, Rizvi N H, Taylor J R and Shestakov A V. Continuous-wave mode-locked Cr4+:YAG laser. Optics Letters 1993; 18:39-41.
59. Sennaroglu A, Pollock C R and Nathel H. Efficient continuous-wave chromium-doped YAG laser. Journal of the Optical Society of America B 1995; 12:930-937.
60. Bouma B, Gouveia-Neto A, Izatt J A, Russell J, Sierra R, Keller U and Fujimoto J G. Hybrid mode locking of a flash-lamp-pumped Ti:Al2O3 laser. Optics Letters 1994; 19:1858-1860.
61. Bouma B, Tearney G J, Boppart S A, Hee M R, Brezinski M E and Fujimoto J G. High-resolution optical coherence tomographic imaging using a mode-locked Ti:Al2O3 laser source. Optics Letters 1995; 20:1486-1488.
62. Bouma B E and Fujimoto J G. Compact Kerr-lens mode-locked resonators. Optics Letters 1996; 21:134-136.
63. Bouma B E, Nelson L E, Tearney G J, Jones D J, Brezinski M E and Fujimoto J G. Optical coherence tomographic imaging of human tissue at 1.55 µm and 1.81 µm using Er and Tm-doped fiber sources. Journal of Biomedical Optics 1998; 3:76-79.
64. Bouma B E, Ramaswamy-Paye M and Fujimoto J G. Compact resonator designs for mode-locked solid-state lasers. Applied Physics B (Lasers and Optics) 1997; 65:213-220.
65. Bouma B E, Tearney G J, Bilinsky I P, Golubovic B and Fujimoto J G. Self-phase-modulated Kerr-lens mode-locked Cr:forsterite laser source for optical coherence tomography. Optics Letters 1996; 21:1839-1841.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with and/or implement any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. A process for obtaining information associated with at least one portion of a biological sample, comprising:
   receiving at least one first electro-magnetic radiation provided from a section near or in the at least one portion of the biological sample; and
   identifying a deformation of the section at a plurality of depths as a function of at least one temperature change within the section and at least one of (i) a phase of at least one second electro-magnetic radiation provided from the section, or (ii) a rate of change of at least one of the phase or an amplitude of the at least one second electro-magnetic radiation.

2. The process according to claim 1, further comprising:
   generating an interferometric signal associated with the at least one second electro-magnetic radiation; and
   determining the phase of the at least one second electro-magnetic radiation using the interferometric signal.

3. The process according to claim 2, further comprising measuring the interferometric signal as a function of a wavelength of the at least one second electro-magnetic radiation.

4. The process according to claim 1, wherein the at least one first electro-magnetic radiation has a wavelength that varies over time.

5. The process according to claim 1, wherein the temperature change is caused using a laser arrangement.

6. The process according to claim 1, further comprising defining a border between at least one irreversibly changed portion and an unchanged portion of the biological sample as a function of the information associated with the deformation.

7. The process according to claim 6, wherein the at least one changed portion is at least one of denatured, damaged or coagulated.

8. The process according to claim 1, further comprising:
   generating an interferometric signal associated with the at least one second electro-magnetic radiation; and
   determining the amplitude of the at least one second electro-magnetic radiation using the interferometric signal.

9. The process according to claim 8, further comprising measuring the interferometric signal as a function of a modifiable wavelength of the at least one second electro-magnetic radiation.

10. The process according to claim 1, wherein the electro-magnetic radiation is forwarded to the section in the sample at a particular wavelength; and further comprising:
    during the forwarding of the at least one first electro-magnetic radiation, controlling a temperature distribution in the sample by modifying the particular wavelength of the electro-magnetic radiation.

11. The process according to claim 1, wherein the forwarding step comprises applying a beam of the electro-magnetic radiation to the section, wherein a cross-sectional area of the beam is at most about $1/10^{th}$ of an entire area of the section, and further comprising:
    applying the beam to the at least one portion at least one of (i) while modulating a wavelength of the laser radiation, or (ii) while monitoring a depth of the application of the laser radiation.

12. A process for controlling a temperature distribution in a sample, comprising:

a) providing an electro-magnetic radiation to a section in the sample at a particular wavelength; and
b) during step (a), controlling the temperature distribution by modifying the particular wavelength of the electro-magnetic radiation.

13. The process according to claim 12, further comprising:
c) identifying a deformation of the at least one portion at a plurality of depths as a function of at least one of (i) a phase of at least one further electro-magnetic radiation provided from the at least one portion, or (ii) a rate of change of at least one of the phase or an amplitude of the at least one further electro-magnetic radiation.

14. The process according to claim 12, wherein step (b) comprises applying a beam of the electro-magnetic radiation to the section, wherein a cross-sectional area of the beam is at most about $\frac{1}{10}^{th}$ of an entire area of the section, and further comprising:
d) applying the beam to the at least one portion at least one of (i) while modulating a wavelength of the laser radiation, or (ii) while monitoring a depth of the application of the laser radiation.

15. The process according to claim 12, wherein the modification to the particular wavelength changes a distribution of damage in at least one portion of the sample.

16. The process according to claim 12, wherein the temperature distribution is further controlled by modifying a power of the electro-magnetic radiation.

17. The process according to claim 12, wherein the particular wavelength is modified to be in a range of approximately at least one of (i) about 1.35 µm to 1.5 µm or (ii) about 1.7 µm to 2.2 µm.

18. The process according to claim 12, wherein the temperature distribution is substantially due to an absorption of the electro-magnetic radiation by water.

19. The process according to claim 12, wherein the electro-magnetic radiation is provided by at least one of a thulium laser amplifier arrangement or an erbium laser amplifier arrangement.

20. The process according to claim 12, wherein a rate at which the particular wavelength is modified is greater that about 10 nm per second.

21. The process according to claim 12, wherein the particular wavelength is modified in a non-random manner.

22. A system for obtaining information associated with at least one portion of a biological sample, comprising:
a first arrangement;
configured to receive at least one first electro-magnetic radiation provided from a section near or in the at least one portion of the biological sample; and
a second arrangement configured to identify a deformation of the section at a plurality of depths as a function of at least one temperature change within the section and at least one of (i) a phase of at least one second electro-magnetic radiation provided from the section, or (ii) a rate of change of at least one of the phase or an amplitude of the at least one second electro-magnetic radiation.

23. The system according to claim 22, wherein a border is defined between at least one changed portion and an unchanged portion of the sample as a function of the information associated with the deformation.

24. The system according to claim 23, wherein the at least one changed portion is at least one of denatured, damaged or coagulated.

25. A system for controlling a temperature distribution in a sample, comprising:
at least one first arrangement which is configured to provide an electro-magnetic radiation to a section in the sample at a particular wavelength; and
at least one first arrangement which is configured to control the temperature distribution by modifying the particular wavelength of the electro-magnetic radiation when the electro-magnetic radiation is provided to the section.

* * * * *